(12) United States Patent
Joung et al.

(10) Patent No.: US 12,013,395 B2
(45) Date of Patent: Jun. 18, 2024

(54) SERODIAGNOSTIC TESTING DEVICE AND SYSTEM FOR EARLY-STAGE LYME DISEASE USING A MULTIPLEXED IMMUNOASSAY

(71) Applicant: THE REGENTS OF THE UNIVERSITY OF CALIFORNIA, Oakland, CA (US)

(72) Inventors: Hyou-Arm Joung, Los Angeles, CA (US); Zachary S. Ballard, Los Angeles, CA (US); Omai Garner, Los Angeles, CA (US); Dino Di Carlo, Los Angeles, CA (US); Aydogan Ozcan, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 668 days.

(21) Appl. No.: 17/285,906

(22) PCT Filed: Oct. 18, 2019

(86) PCT No.: PCT/US2019/057072
§ 371 (c)(1),
(2) Date: Apr. 15, 2021

(87) PCT Pub. No.: WO2020/082029
PCT Pub. Date: Apr. 23, 2020

(65) Prior Publication Data
US 2021/0382052 A1    Dec. 9, 2021

Related U.S. Application Data

(60) Provisional application No. 62/910,973, filed on Oct. 4, 2019, provisional application No. 62/747,300, filed on Oct. 18, 2018.

(51) Int. Cl.
*G01N 33/569* (2006.01)
*B01L 3/00* (2006.01)
(Continued)

(52) U.S. Cl.
CPC .. *G01N 33/56911* (2013.01); *B01L 3/502715* (2013.01); *B01L 2300/0819* (2013.01);
(Continued)

(58) Field of Classification Search
CPC ..... B01L 2300/0819; B01L 2300/0887; B01L 2300/126; B01L 2400/0406;
(Continued)

(56) References Cited

U.S. PATENT DOCUMENTS 8,916,390 B2   12/2014   Ozcan
2012/0015824 A1   1/2012   Love et al.
(Continued)

FOREIGN PATENT DOCUMENTS

WO   WO 1999/053288   10/1999
WO   WO 2016/205736   12/2016
(Continued)

OTHER PUBLICATIONS

Mohammed Alasel et al., Promising alternatives for one-tier testing of Lyme borreliosis, Clinica Chimica Acta 479 (2018) 148-154.
(Continued)

*Primary Examiner* — Jennifer Wecker
(74) *Attorney, Agent, or Firm* — VISTA IP LAW GROUP LLP

(57) ABSTRACT

A multiplexed vertical flow serodiagnostic testing device for diseases such as Lyme disease includes one or more multi-piece cassettes that include vertical stacks of functionalized porous layers therein. A bottom piece of the cassette includes a sensing membrane with a plurality of spatially multiplexed immunoreaction spots or locations. Top pieces are used to
(Continued)

deliver sample and/or buffer solutions along with antibody-conjugated nanoparticles for binding with the immunoreaction spots or locations. A colorimetric signal is generated by the nanoparticles captured on the sensing membrane containing disease-specific antigens. The sensing membrane is imaged by a cost-effective portable reader device. The images captured by the reader device are subject to image processing and analysis to generate positive (+) or negative (−) indication for the sample. A concentration of one or more biomarkers may also be generated. The testing device is rapid, simple, inexpensive, and allows for simultaneous measurement of multiple antibodies and/or antigens making it an ideal point-of-care platform for disease diagnosis.

24 Claims, 24 Drawing Sheets

(51) Int. Cl.
    *B82Y 5/00*     (2011.01)
    *B82Y 30/00*     (2011.01)
    *B82Y 40/00*     (2011.01)

(52) U.S. Cl.
    CPC . *B01L 2300/126* (2013.01); *B01L 2400/0406* (2013.01); *B82Y 5/00* (2013.01); *B82Y 30/00* (2013.01); *B82Y 40/00* (2013.01); *G01N 2333/20* (2013.01)

(58) Field of Classification Search
    CPC ... B01L 3/502715; B82Y 30/00; B82Y 40/00; B82Y 5/00; G01N 2333/20; G01N 33/523; G01N 33/526; G01N 33/56911
    See application file for complete search history.

(56) References Cited

U.S. PATENT DOCUMENTS

| | | | |
|---|---|---|---|
| 2012/0065912 | A1 | 3/2012 | Corkan et al. |
| 2014/0120563 | A1 | 5/2014 | Ozcan |
| 2017/0336398 | A1 | 11/2017 | Lin et al. |
| 2018/0246085 | A1* | 8/2018 | Siciliano ............ B01L 3/5023 |

FOREIGN PATENT DOCUMENTS

| | | | | |
|---|---|---|---|---|
| WO | WO 2017/024297 | | 2/2017 | |
| WO | WO-2017024297 | A1 * | 2/2017 | ........ B01L 3/502707 |
| WO | WO 2018/138139 | | 8/2018 | |

OTHER PUBLICATIONS

Elif Burcu Bahadır et al., Lateral flow assays: Principles, designs and labels, Trends in Analytical Chemistry 82 (2016) 286-306.

John A. Branda et al., Advances in Serodiagnostic Testing for Lyme Disease Are at Hand, Viewpoints, CID, 2018:66 (Apr. 1), 1133-1139.

Can Dincer et al., Multiplexed Point-of-Care Testing—xPOCT, Trends Biotechnol. Aug. 2017; 35(8): 728-742.

Wenyan Hong et al., Development of an up-converting phosphor technology-based 10-channel lateral flow assay for profiling antibodies against Yersinia pestis, Journal of Microbiological Methods, 83, (2010), 133-140.

Minseok S. Kim et al., Breast Cancer Diagnosis Using a Microfluidic Multiplexed Immunohistochemistry Platform, PLoS One 5(5): e10441, doi:10.1371/journal.pone.0010441.

Chen-zhong Li et al., Paper based point-of-care testing disc for multiplex whole cell bacteria analysis, Biosensors and Bioelectronics, 26, (2011), 4342-4348.

Jia Li et al., Multiplex lateral flow detection and binary encoding enables a molecular colorimetric 7-segment display, Lab Chip, 2016, 16, 242.

Jia Li et al., Multiplexedlateral flowbiosensors:Technologicaladvances for radicallyimprovingpoint-of-carediagnoses, Biosensors and Bioelectronics, 83, (2016), 177-192.

Andres W. Martinez et al., Diagnostics for the Developing World: Microfluidic Paper-Based Analytical Devices, Anal. Chem. 2010, 82, 3-10.

Andrew Moore et al., Current Guidelines, Common Clinical Pitfalls, and Future Directions for Laboratory Diagnosis of Lyme Disease, United States, Emerging Infectious Diseases, www.cdc.gov/eid, vol. 22, No. 7, Jul. 2016, 1169-1177.

Samiksha Nayak et al., Microfluidics-based point-of-care test for serodiagnosis of Lyme Disease, Scientific Reports, 6:35069, DOI: 10.1038/srep35069.

Geertruida A. Posthuma-Trumpie et al., Lateral flow (immuno)assay: its strengths, weaknesses, opportunities and threats. A literature survey, Anal Bioanal Chem (2009) 393:569-582, DOI 10.1007/s00216-008-2287-2.

Muhammad Sajid et al., Designs, formats and applications of lateral flow assay: A literature review, Journal of Saudi Chemical Society (2015) 19, 689-705.

Basil H. Shadfan et al., A multiplexable, microfluidic platform for the rapid quantitation of a biomarker panel for early ovarian cancer detection at the point-of-care, Cancer Prev Res (Phila), Jan. 2015, 8(1): 37-48, doi:10.1158/1940-6207.CAPR-14-0248.

Henk L. Smits et al., Lateral-Flow Assay for Rapid Serodiagnosis of Human Leptospirosis, Clinical and Diagnostic Laboratory Immunology, vol. 8, No. 1, Jan. 2001, p. 166-169.

Mingzhu Yang et al., Inkjet-printed barcodes for a rapid and multiplexed paper-based assay compatible with mobile devices, Lab Chip, 2017, 17, 3874.

PCT International Search Report and Written Opinion for PCT/US2019/057072 dated Jan. 14, 2020, Applicant: The Regents of the University of California (17 pages).

PCT International Preliminary Report on Patentability (Chapter I of the Patent Cooperation Treaty) for PCTUS2019/057072, Applicant: The Regents of the University of California, Form PCT/IB/326 and 373, dated Apr. 29, 2021 (15 pages).

* cited by examiner

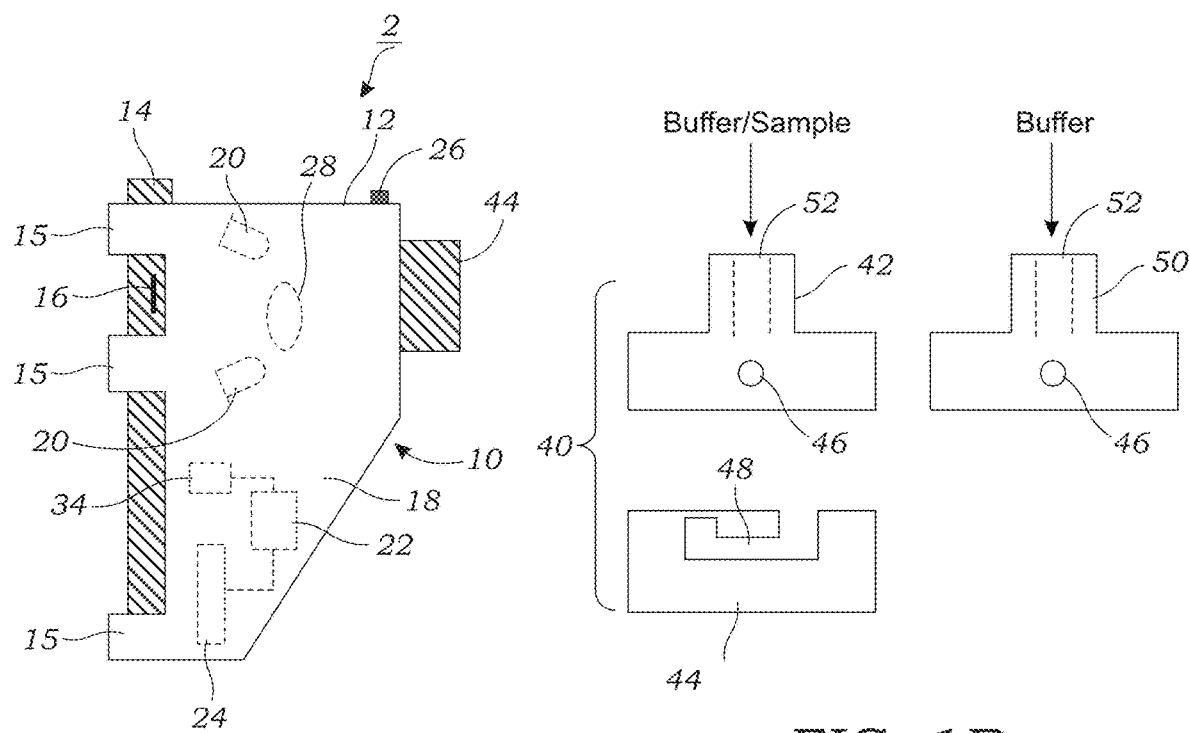
FIG. 1A
FIG. 1B
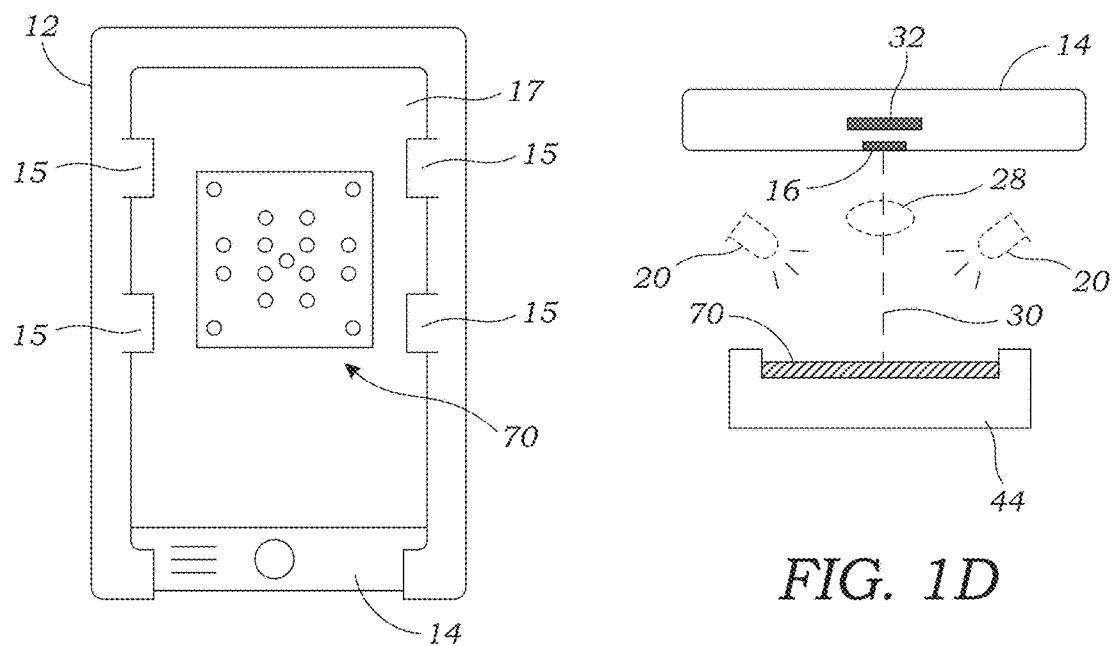
FIG. 1C
FIG. 1D

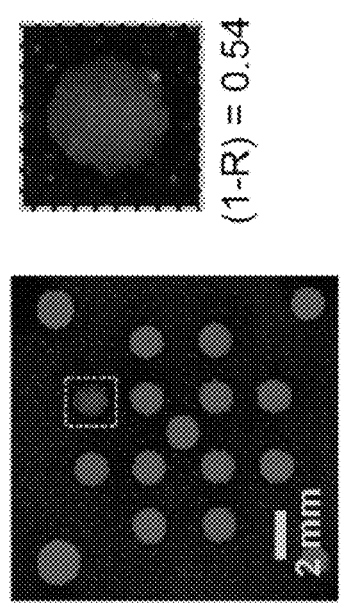
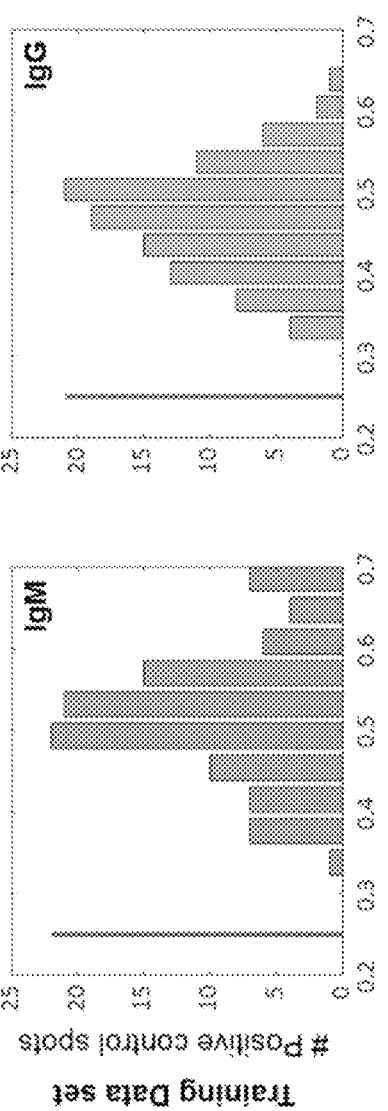
FIG. 11A  FIG. 11B  FIG. 11C
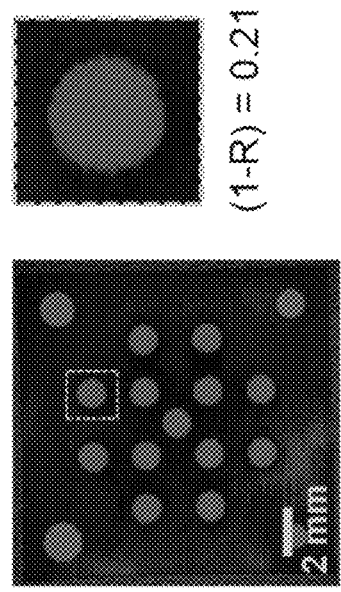
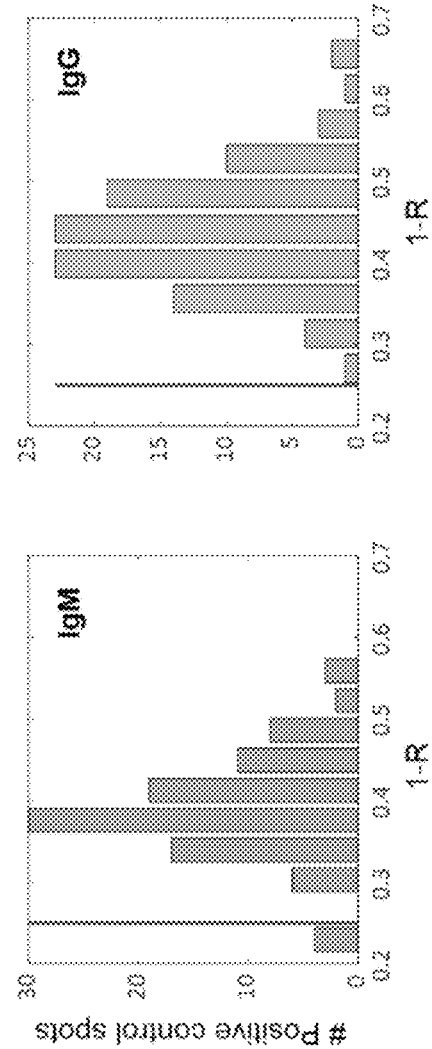
FIG. 11D  FIG. 11E  FIG. 11F

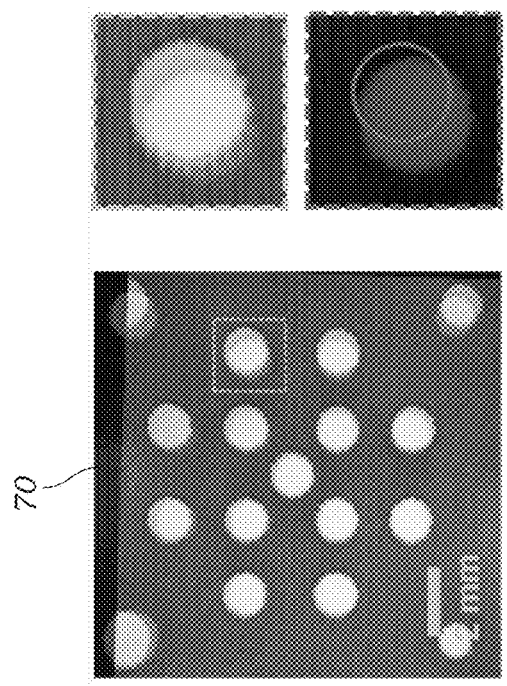
FIG. 12A
FIG. 12B
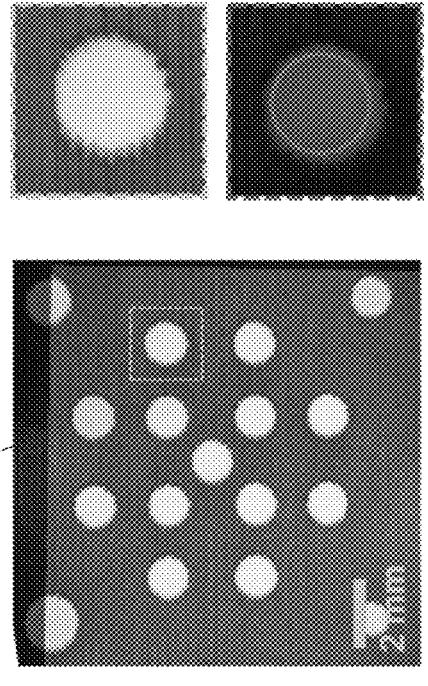
FIG. 12C
FIG. 12D
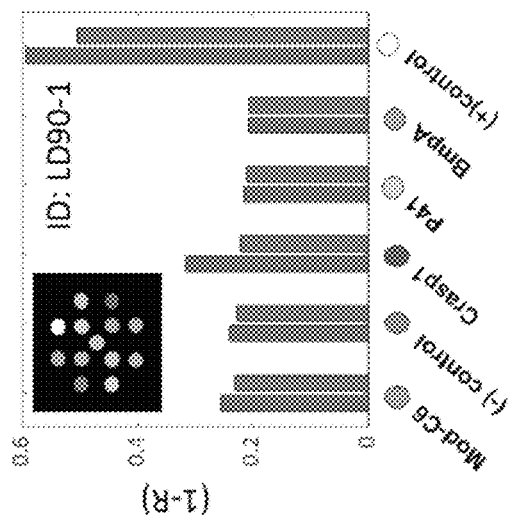
FIG. 12E

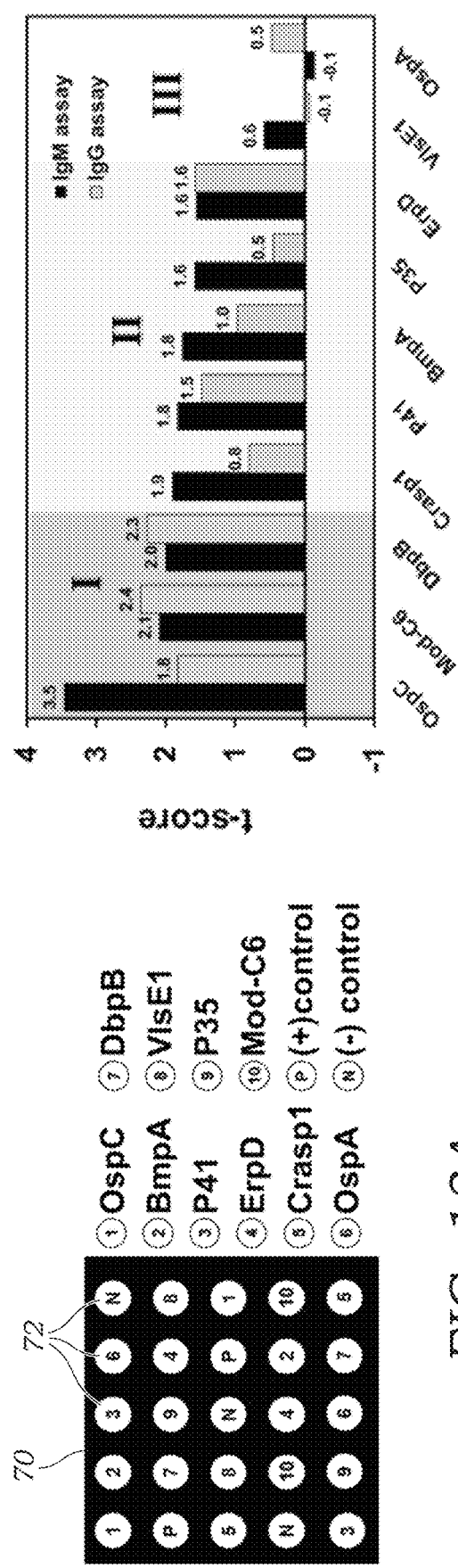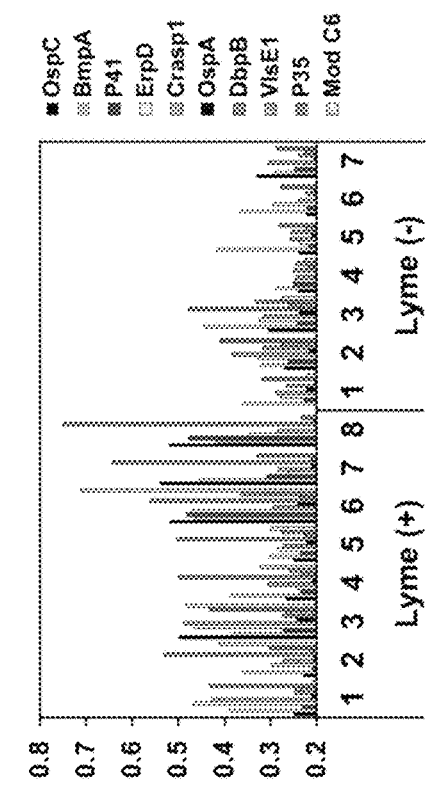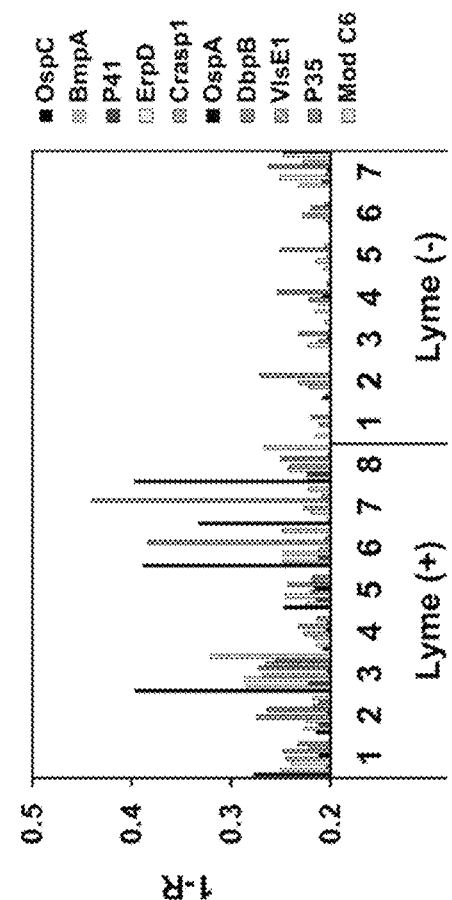
FIG. 13A  FIG. 13B  FIG. 13C  FIG. 13D

|  | POC User | $\dfrac{TP}{TP+FN}$ | Network output (mean ± std. dev.) |
|---|---|---|---|
| LD Case #1 | Operator A | 6/6 | 0.997 ± 0.003 |
| LD Case #2 | Operator A | 4/6 | 0.652 ± 0.445 |
| LD Case #3 | Operator A,B,C | 6/6 | 0.947 ± 0.120 |

|  | POC User | $\dfrac{TN}{TN+FP}$ | Network output (mean ± std. dev.) |
|---|---|---|---|
| Endemic Control #1 | Operator A | 6/6 | 0.139 ± 0.221 |
| Endemic Control #2 | Operator A | 6/6 | 0.045 ± 0.088 |
| Endemic Control #3 | Operator A,B,C | 5/6 | 0.265 ± 0.423 |

*FIG. 16*

| CV(%) | | OspC | DbpB | Mod-C6 | ErpD | P41 | BmpA | Crasp1 | P35 | Neg | Pos |
|---|---|---|---|---|---|---|---|---|---|---|---|
| IgM | Positive | POS1 | 31.7% | 3.0% | 5.9% | 7.5% | 4.0% | 11.0% | 9.3% | 12.0% | 10.4% | 10.1% |
| | | POS2 | 15.5% | 14.6% | 3.0% | 6.4% | 7.1% | 6.3% | 5.5% | 4.8% | 4.8% | 13.1% |
| | Negative | Control1 | 4.6% | 11.0% | 3.3% | 5.8% | 6.3% | 11.6% | 4.7% | 3.8% | 5.0% | 7.0% |
| | | Control2 | 8.5% | 7.9% | 3.7% | 3.7% | 6.2% | 6.5% | 8.0% | 9.1% | 5.0% | 9.9% |
| IgG | Positive | POS1 | 10.8% | 13.0% | 6.0% | 14.9% | 24.7% | 21.9% | 8.8% | 8.0% | 6.2% | 13.0% |
| | | POS2 | 8.5% | 12.1% | 7.1% | 6.2% | 9.9% | 8.7% | 10.9% | 7.1% | 9.9% | 10.2% |
| | Negative | Control1 | 4.9% | 5.7% | 6.2% | 7.4% | 8.0% | 13.0% | 7.4% | 10.8% | 5.4% | 15.2% |
| | | Control2 | 2.9% | 10.3% | 8.5% | 6.9% | 7.4% | 18.4% | 10.1% | 7.0% | 3.7% | 14.5% |

*FIG. 17C*

| Average CV (%) | IgM | IgG |
|---|---|---|
| (+) | 9.3% | 10.9% |
| (−) | 6.6% | 8.7% |

*FIG. 17D*

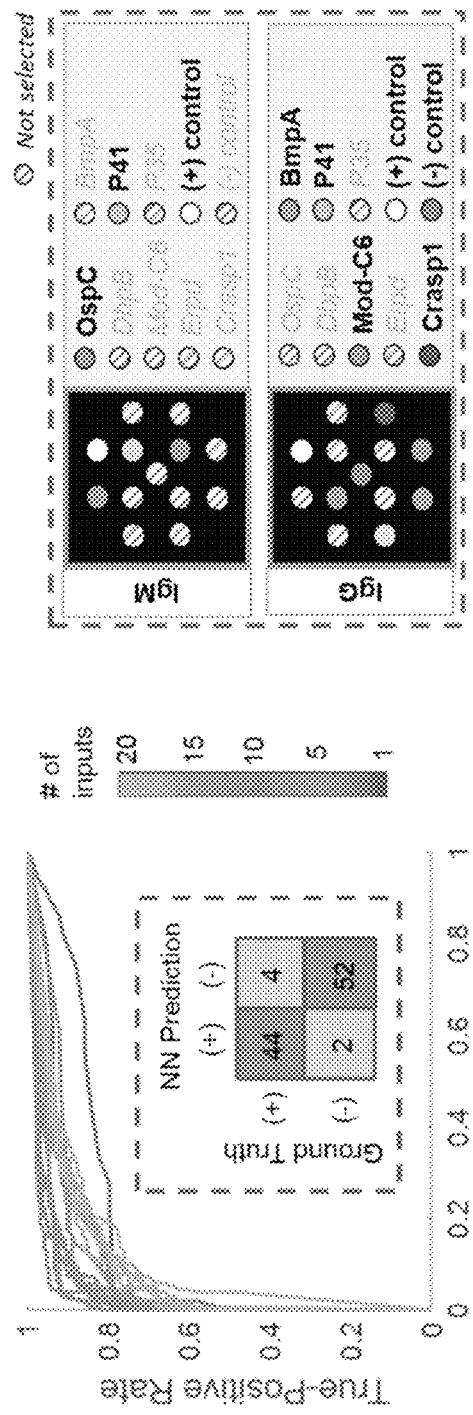
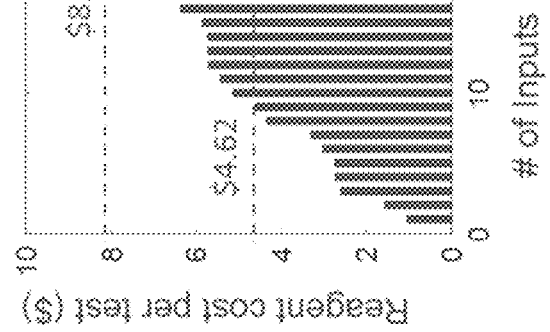
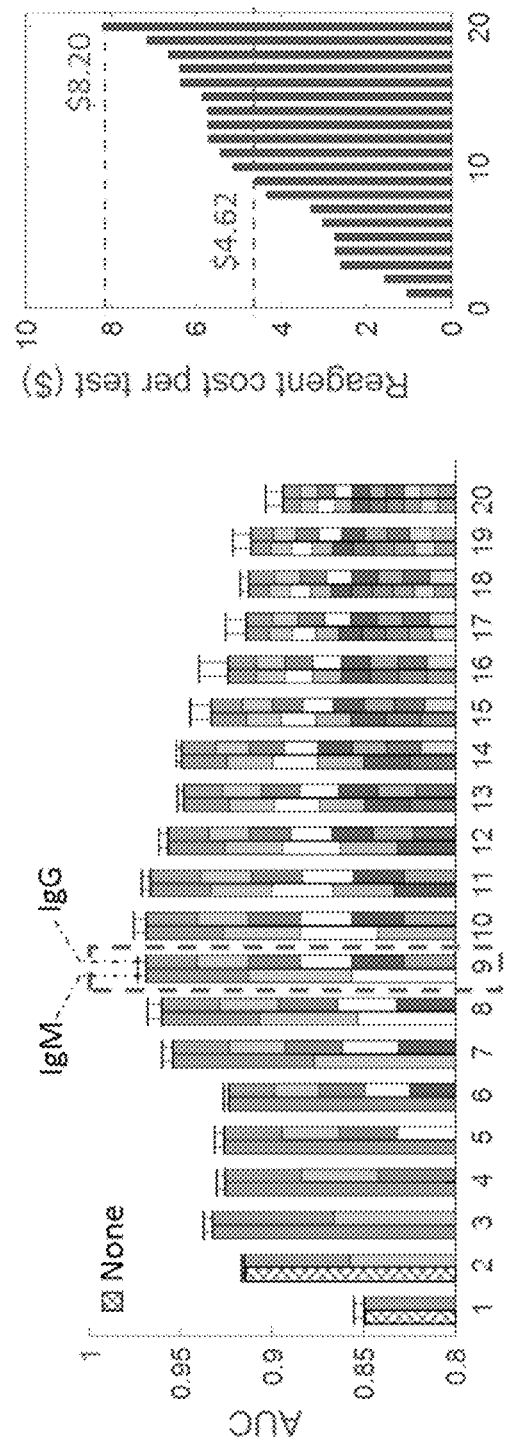
FIG. 18A
FIG. 18B
FIG. 18C
FIG. 18D

SERODIAGNOSTIC TESTING DEVICE AND SYSTEM FOR EARLY-STAGE LYME DISEASE USING A MULTIPLEXED IMMUNOASSAY

RELATED APPLICATIONS

This Application is a U.S. National Stage filing under 35 U.S.C. § 371 of International Application No. PCT/US2019/057072, filed Oct. 18, 2019, which claims priority to U.S. Provisional Patent Application Nos. 62/747,300 filed on Oct. 18, 2018 and 62/910,973 filed on Oct. 4, 2019, which are hereby incorporated by reference. Priority is claimed pursuant to 35 U.S.C. §§ 119, 371 and any other applicable statute.

STATEMENT REGARDING FEDERALLY SPONSORED RESEARCH OR DEVELOPMENT

This Application is a U.S. National Stage filing under 35 U.S.C. § 371 of International Application No. PCT/US2019/057072, filed Oct. 18, 2019, which claims priority to U.S. Provisional Patent Application Nos. 62/747,300 filed on Oct. 18, 2018 and 62/910,973 filed on Oct. 4, 2019, which are hereby incorporated by reference. Priority is claimed pursuant to 35 U.S.C. §§ 119, 371 and any other applicable statute.

TECHNICAL FIELD

The technical field generally relates to vertical flow immunodiagnostic assays. More particularly, the technical field relates a multiplexed vertical flow immunodiagnostic assay (xVFA) that is used in conjunction with a mobile reader device. As illustrated herein, in one particular application the assay and reader are used to detect antibodies in Lyme disease.

BACKGROUND

Lyme disease (LD) is the most common vector-borne infectious disease in both North America and Europe, causing ~300,000 infections annually in the United States. It is caused by infection with the spirochete *Borrelia burgdorferi* (Bb) transmitted by black-legged ticks (*Ixodes* genus). Early disease is associated with a characteristic skin lesion, erythema migrans (EM) along with other symptoms. If not diagnosed and treated with appropriate antibiotics, the infection can disseminate to distal sites including the nervous system, heart, and joints causing an array of symptoms, including e.g., lymphocytic meningitis, cranial neuropathy, facial nerve palsy, radiculopathy, A/V node heart block, and arthritis.

Although a presenting EM is diagnostic, the characteristic lesion is absent in 10-20% of infected persons and is frequently atypical thus escaping recognition. This makes laboratory testing critical to confirm the diagnosis and guide treatment. Despite recent advances in direct detection of Bb through e.g. Nucleic Acid Amplification Testing (NAAT), these methods remain inadequate due to the low concentration and transient presence of Bb in the blood. Culturing Bb is also not practical due to the slow growth of the bacteria, as well as the need for specialized growth media. Therefore, current testing methods work indirectly by detecting specific antibodies produced by the body's immune response to the infection.

The United States Center for Disease Control and Prevention (CDC) recommends a 'two-tier' testing method, where the first-tier consists of a sensitive Enzyme Immunoassay (EIA) or immunofluorescence assay (IFA). If the first-tier is positive or equivocal, a Western Blot (WB) is then recommended for confirming the presence of 2 of 3 Immunoglobulin M (IgM) antibodies and/or 5 of 10 Immunoglobulin G (IgG) antibodies targeting Bb associated antigens. A number of reports have also showed the efficacy of a modified two-tier test (MTTT) format, where the WB is replaced by a second complimentary EIA, and as a result, the FDA has recently approved the use of some EIAs as viable tests for the second tier.

Despite being the standard for the laboratory diagnosis of LD, the two-tier serological testing method has multiple drawbacks. Although there is a high specificity (>98%) and sensitivity (70-100%) in late LD, the two-tier test has poor sensitivity in early-stage LD, seldom exceeding 50% at the time when most patients seek medical care. This is also the time when treatment is the least costly and most effective at preventing disease sequela. The poor sensitivity can be attributed to the underdeveloped immune response within the first weeks of infection in which a limited IgM antibody response is followed by an IgG antibody response. However, it is also exacerbated by the limited number of antigen-targets in the first tier test that may miss detection of antibodies produced during the earliest stage of infection. Specifically, the earliest responses are to Flagellin B (FlaB) and p66 with responses to a number of additional antigens such as *Borrelia burgdorferi* antigens: OspC (25 kd), VlsE, BBK32, FlaA (37 kd), BmpA (39 kd) and DbpA proteins developing as *B. burgdorferi* disseminates.

The two-tier testing method also suffers from slow turn-around time (>24 hours) and high costs (>$400/test), with estimated expenses exceeding $492 million annually just in the United States. Additionally, the standard testing used in the two-tier format must be performed in a centralized testing facility by trained technicians, requiring bulky and expensive clinical analyzers. These drawbacks therefore limit accessibility to accurate LD testing, especially impacting populations far from clinical laboratories as well as populations in rural and forested areas where tick bites are prevalent. Therefore, accurate and affordable LD testing methods for use at the point-of-care (POC) are in high demand.

Paper-based lateral flow assays (LFAs), also known as Rapid Diagnostic Tests (RDTs), are appealing for POC serological analysis due to their low-cost, ease-of-use, and rapid nature. These tests use e.g., colorimetric or fluorescent conjugates embedded in one-time-use cassettes to rapidly and cost-effectively detect the presence of antibodies specific to disease. LFAs however, are not conducive to the detection of multiple analytes due to their in-line geometry, measuring only one or two antibodies in a single test. This restrictive design inherently limits the potential sensitivity and specificity of traditional RDTs for LD. For example, tests that rely on single antibody measurements (like many EIAs in the first tier) can be less robust to false positive results due to antigens (p66 and FlaB in particular) which contain epitopes that are highly cross-reactive with epitopes found in multiple other bacteria. They can also have low sensitivity if the target antigen is mismatched with the underlying immunodominance. This paradigm is the reason that the performance of the two-tier testing protocol can depend on which EIA is used in the first tier, as well as what strain of Bb the EIA test was designed against, B31 being the most common. To overcome this limitation, large-scale screening efforts alongside new epitope mapping and peptide synthesis are focused on developing a universal multi-antigen detection panel, with e.g., 5 to 10 LD-specific antigen targets being suggested for improving diagnostic performance for early LD.

SUMMARY

In one embodiment, a multiplexed immunodiagnostic assay device and system is disclosed for that is powered by deep learning for serological diagnosis of early-stage LD. The assay device and system include a multiplexed vertical flow assay (xVFA) device, that includes of a stack of functional porous layers (e.g., paper in one embodiment), which in contrast to the more common LFA, allows for a multi-antigen detection panel for measuring an array of LD-specific antibodies on a single sensing membrane. In one particular implementation, the sensing membrane contains thirteen (13) spatially-separated immunoreaction spots, the sensing membrane being functionalized with Bb-specific antigens (OspC, BmpA, P41, DbpB, Crasp1, P35, Erpd/Arp37) as well as a peptide (Mod-C6) composed of a C6-like epitope linked to a specific p41 epitope. The xVFA can be operated in about 15 min, after which the assay cassette is opened and the sensing membrane is imaged by a portable reader device. The portable reader device may, in one embodiment, be secured to a separate portable electronic device such as a mobile phone (e.g., Smartphone) that uses the internal camera to image the sensing membrane in conjunction with an opto-mechanical attachment. Computational analysis then quantifies the colorimetric signals on the sensing membrane through automated image processing, and a trained neural network is used to automatically infer a diagnosis from the multiplexed immunoreactions or output a concentration or concentration range of one or more biomarkers.

In some embodiments, the trained neural network is omitted and a pixel intensity statistic or normalized pixel intensity value is calculated for each spot or location on the sensing membrane using the acquired images obtained by the portable reader device. The pixel intensity statistics or normalized pixel intensity values for the spots or locations may then be compared to threshold values to generate or output a diagnosis or a concentration/concentration range for one or more biomarkers.

For the embodiment that utilizes the trained neural network, the diagnostic algorithm in was trained with fifty (50) human serum samples (25 early-stage LD and 25 endemic controls), obtained from the Lyme Disease Biobank (LDB), run in duplicate for both IgM and IgG antibodies, resulting in 200 individually-activated xVFAs composing the training data-set. This training data-set was also used to computationally select a subset of detection antigens from the larger panel using a feature selection technique, improving the diagnostic performance and reducing the per-test cost. The computational xVFA was evaluated through blind testing of an additional fifty (50) human serum samples (25 early stage LD and 25 endemic controls), obtained fully-blinded by the LDB. Testing entirely early-stage LD samples, the device and system achieved an AUC of 0.95, and by equally weighing the false positive and false negative results, a sensitivity and specificity of 90.5% and 87.0%, respectively, were obtained with regard to the gold-standard two-tier serological testing. By adjusting the diagnostic cut-off value to favor high-specificity during the training phase and incorporating batch-specific standardization for the network inputs, the blind testing specificity improved to 96.3%, with a small drop in our sensitivity (85.7%) in relation to the gold-standard two-tier serological testing. Development of a POC two-tier replacement test will allow for more rapid diagnosis and better treatment outcomes. This is especially important as LD is projected to increase over the next decades as the geographic areas of tick-populations continue to expand. The system and device disclosed herein demonstrates a leapfrog improvement over existing POC LD testing approaches, reporting a cost-effective and rapid (15 min) paper-based multiplexed assay powered by deep learning for serological diagnosis of early-stage LD for POC applications.

In one embodiment, a multiplexed immunodiagnostic assay device includes one or more cassettes each cassette having a lower portion, a first upper portion and a second upper portion, wherein the lower portion of the one or more cassettes contains a sensing membrane having a plurality of immunoreaction spots or locations formed therein, and wherein the first upper portion and the second upper portion are each detachably connected to the lower portion of the one or more cassettes and configured to receive a sample or assay solution, wherein the first upper portion comprises a stack of discrete porous layers including one or more vertical flow diffuser layers and wherein the second upper portion comprises a stack of discrete porous layers including at least one conjugation pad layer holding antibody-conjugated nanoparticles therein. A portable reader device is used with the device and includes one or more illumination sources and at least one processor or control circuitry, a camera, wherein the one or more illumination sources configured to illuminate the sensing membrane in the lower portion of the one or more cassettes and the camera captures color or monochrome images of the sensing membrane.

In another embodiment, a method of using the multiplexed immunodiagnostic assay device includes securing the first upper portion to the lower portion of one of the one or more cassettes; flowing one or more buffer solutions into an inlet of the first upper portion along with a solution containing the sample; removing the first upper portion from the lower portion; securing the second upper portion to the lower portion; flowing a buffer or wash solution into an inlet of the second upper portion; removing the second upper portion from the lower portion; inserting the lower portion with the sensing membrane into or onto the portable reader device; illuminating the sensing membrane and capturing one or more color or monochrome images of the sensing membrane; subjecting the captured one or more color or monochrome images to image processing with a computing device or at least one processor to generate a normalized pixel intensity value or k/s statistic for the immunoreaction spots or locations on the sensing membrane; and outputting a result indicating a positive (+) or negative (−) classification for the sample based on the k/s statistic for the immunoreaction spots or locations on the sensing membrane.

In another embodiment, a method of using the multiplexed immunodiagnostic assay device includes securing the first upper portion to the lower portion of one of the one or more cassettes; flowing one or more buffer solutions into an inlet of the first upper portion along with a solution containing the sample; removing the first upper portion from the lower portion; securing the second upper portion to the lower portion; flowing a buffer or wash solution into an inlet of the second upper portion; removing the second upper portion from the lower portion; inserting the lower portion with the sensing membrane into or onto the portable reader device; illuminating the sensing membrane and capturing one or more color or monochrome images of the sensing membrane; subjecting the captured one or more color or monochrome images to image processing with a computing device to generate normalized pixel intensity values for one or more of the immunoreaction spots or locations; inputting the normalized pixel intensity values for the one or more of the immunoreaction spots or locations to a trained neural network configured to receive the same to a trained neural network configured to output a concentration of at least one disease marker of interest.

In another embodiment, a method of using the multiplexed immunodiagnostic assay device includes securing the first upper portion to the lower portion of one of the one or more cassettes; flowing one or more buffer solutions into an inlet of the first upper portion along with a solution containing the sample; removing the first upper portion from the lower portion; securing the second upper portion to the lower portion; flowing a buffer or wash solution into an inlet of the second upper portion; removing the second upper portion from the lower portion; inserting the lower portion with the sensing membrane into or onto the portable reader device; illuminating the sensing membrane and capturing one or more color or monochrome images of the sensing membrane; subjecting the captured one or more color or monochrome images to image processing with a computing device to generate normalized pixel intensity values for one or more of the immunoreaction spots or locations; and inputting the normalized pixel intensity values for the one or more of the immunoreaction spots or locations to a trained neural network configured to receive the same to a trained neural network configured to output a concentration of at least one disease marker of interest.

In another embodiment, a multiplexed immunodiagnostic assay device includes one or more cassettes each cassette having a lower portion and an upper portion, wherein the lower portion of the one or more cassettes contains a sensing membrane having a plurality of immunoreaction spots or locations formed therein, and wherein the upper portion are detachably connected to the lower portion of the one or more cassettes and configured to receive a sample and/or assay solution, wherein the upper portion comprises a stack of discrete porous layers including at least one absorption layer, one or more vertical flow diffuser layers, one or more spreading layers, at least one conjugation pad layer holding antibody-conjugated nanoparticles therein, and at least one supporting layer. The assay device is used in conjunction with a portable reader device having one or more illumination sources and at least one processor or control circuitry, a camera, wherein the one or more illumination sources configured to illuminate the sensing membrane in the lower portion of the one or more cassettes and the camera captures color or monochrome images of the sensing membrane.

In another embodiment, a method of using the multiplexed immunodiagnostic assay device includes securing the upper portion to the lower portion of one of the one or more cassettes; flowing one or more buffer or wash solutions into an inlet of the upper portion along with a solution containing the sample; removing the upper portion from the lower portion; inserting the lower portion with the sensing membrane into or onto the portable reader device; illuminating the sensing membrane and capturing one or more color or monochrome images of the sensing membrane; subjecting the captured one or more color or monochrome images to image processing with a computing device to generate normalized pixel intensity values for one or more of the immunoreaction spots or locations; and inputting the normalized pixel intensity values for the one or more of the immunoreaction spots or locations to a trained neural network configured to receive the same and generate one or more of (i) a confidence score reflective of at least a positive (+) or negative (−) indication for the sample based on a thresholding of the confidence score and/or (ii) a concentration of at least one disease marker of interest.

BRIEF DESCRIPTION OF THE DRAWINGS

FIG. 1A illustrates a side view of the portable reader device along with a cassette (bottom) that is secured to the opto-mechanical attachment. The opto-mechanical attachment is illustrated being secured to a mobile phone having camera functionality.

FIG. 1B illustrates an exemplary cassette that is used to perform the vertical flow immunodiagnostic assay. The cassette includes a bottom or lower portion that holds the sensing membrane having a plurality of immunoreaction spots or locations formed therein. The cassette also includes first and second tops or upper portions that detachably connect to the lower portion via mechanical engagement. The first top portion, which receives a liquid sample (and buffer or other assay reagents or solutions) contains a plurality of discrete porous layers as part of the assay including at least one vertical flow diffuser layer. The second top portion, which receives buffer or other reagents/solutions/washes, also contains a plurality of discrete porous layers as part of the assay including at least one vertical flow diffuser layer and a conjugation pad that contains antibody-conjugated nanoparticles therein.

FIG. 1C illustrates a front facing view of a mobile phone device (e.g., Smartphone) connected to the portable reader device. The screen or display of the mobile phone device illustrates an image of the sensing membrane that was obtained with the camera of the mobile phone.

FIG. 1D illustrates a portable electronic device that is arranged to obtain an image of the sensing membrane of the lower/bottom cassette portion. A lens is located in the portable reader device is used to focus/defocus the image of the sensing membrane onto the camera of the portable electronic device. Also illustrated are the light sources (e.g., light emitting diodes (LEDs)).

FIG. 11A illustrates a histogram of the IgM and positive control immunoreaction spots over the training data-set.

FIG. 11B illustrates a histogram of the IgG and positive control immunoreaction spots over the training data-set.

FIG. 11C is an example image taken with the mobile phone reader of a sensing membrane with a working IgM control spot (right).

FIG. 11D is a histogram of the IgM and positive control immunoreaction spots over the blind testing data-set, showing 4 outliers due to fabrication error. These control spot signals are below the test-failure cutoff denoted by the vertical red line at $(1-R)_{FAILURE}=0.25$.

FIG. 11E is a histogram of the IgG and positive control immunoreaction spots over the blind testing data-set.

FIG. 11F is an example image of a sensing membrane with a failed (blank) IgM control spot (right), which does not show any nanoparticle-based binding signal; for comparison also see FIG. 11C for an example of a working IgM control spot.

FIG. 12A is an example of failed image registration between the background and signal image using the rigid transformation. Here the background (before image) and signal (after image) are tinted pink and green respectively and overlaid to better illustrate the degree of misalignment. The inset (upper right) shows the misalignment of a single immunoreaction spot outlined by the dotted line.

FIG. 12B illustrates the circles showing the fixed-radius masks used for sampling the immunoreaction spots on the signal sensing membrane using the misaligned image.

FIG. 12C illustrates the registered background and signal images after applying an affine transformation, which incorporates a scaling factor.

FIG. 12D illustrates the correctly-sampled immunoreaction spots in the sensing membrane after the registration correction.

FIG. 12E shows the (1−R) colorimetric signals of the immunoreaction spots before (left bar graph of pair) and after (right bar graph of pair) the image registration correction. For simplicity, only the immunoreaction signals used as inputs to the final neural network are shown.

FIG. 13A illustrates the spot map for the antigen screening process including 10 capture antigens.

FIG. 13B shows the t-scores (Eq. 2) of the ten (10) antigens in the pre-screening panel. Three regimes are defined (shaded regions); antigens in regime I are given two spots within the testing antigen panel, antigens in regime II are given one spot in the panel, and antigens in regime III are not included in the testing antigen panel.

FIG. 13C illustrates the IgM sensing membrane colorimetric signal for each Lyme positive (left) and Lyme negative (right) human serum sample in the pre-screening cohort.

FIG. 13D illustrates the IgG sensing membrane colorimetric signal for each Lyme positive (left) and Lyme negative (right) human serum sample in the pre-screening cohort.

FIG. 16 illustrates precision testing results of three seropositive samples (top) and three endemic controls (bottom) repeated 6 times and by different operators. Here the inputs to the network were standardized to the mean and standard deviation of the batch of sensors used for precision testing, and a decision threshold of 0.66 was used as determined during the training phase.

FIG. 17C shows the coefficient of variation (% CV) of each immunoreaction spot for the repeated tests.

FIG. 17D is a summary of the % CV over all the immunoreaction spots broken down by the seropositive and seronegative samples as well as the IgM and IgG sensing membrane.

FIG. 18A illustrates the receiver operator characteristic (ROC) curves resulting from the neural network inference during cross validation. The color bar represents the output from networks trained with different number of input features. The inset defined by the red dotted line shows the confusion matrix for all the samples in the training set predicted during cross-validation using the 9 antigen inputs shown in FIG. 18B which is selected based on the optimization reported in FIG. 12C.

FIG. 18B illustrates different input features used to train the neural network.

FIG. 18C illustrates the area-under-the-curve (AUC) plotted for various networks trained with a different number of inputs of the multi-antigen panel (also see (FIG. 18A)). Each bar plot corresponds to the ROC curves shown in A, and is coded to represent which members of the multi-antigen panel are included as the inputs with the left and right side of each bar showing the members from the IgM and IgG sensing membrane, respectively. The dotted line shows the local optimum AUC (0.969) and the resulting nine (9) selected features. The error bars show the standard deviation between four (4) different training instances of the same network.

FIG. 18D is a graph showing the reagent cost of the sensing membrane versus the number of selected members in the multi-antigen panel as they are included in the order shown in FIG. 18C. Under large-volume manufacturing the reagent cost per test is expected to drop by more than an order of magnitude. The lower dotted line ($4.62) represents the reagent cost for the nine (9) selected antigens, and the upper dotted line ($8.20) shows the reagent cost of the whole antigen panel before feature selection.

DETAILED DESCRIPTION OF THE ILLUSTRATED EMBODIMENTS

Figure 1E:
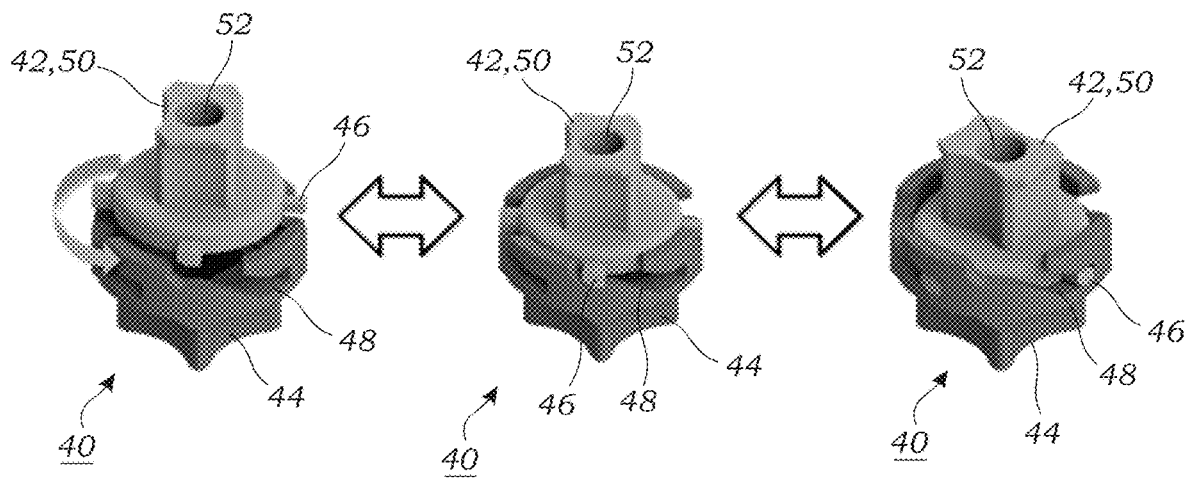
FIG. 1E illustrates a perspective view of a cassette with the top or upper portion being twisted relative to the bottom or lower portion illustrating the detachable nature of the cassette portions. Rotation in a first direction secures the top or upper portion to the bottom or lower portion while rotation in a second, opposite direction is used to remove the top or upper portion from the bottom or lower portion of the cassette.

FIG. 1A illustrates a side view of a multiplexed immunodiagnostic assay device 2 according to one embodiment. The multiplexed immunodiagnostic assay device 2 includes a portable reader device 10 that, in one embodiment, includes an opto-mechanical attachment 12 that is detachably mounted to a portable electronic device 14 having a camera 16 (see also FIG. 1D). The portable electronic device 14 may include a mobile phone or Smartphone such as that illustrated in FIGS. 1A, 1C, and 1D but may also include tablet PCs, a camera, or the like. The opto-mechanical attachment 12 may include a number of tabs, clips, or fasteners 15 that enable the opto-mechanical attachment 12 to be removably secured to the portable electronic device 14. The opto-mechanical attachment 12 may be made from any number of materials including metals, polymers, plastics, and the like. In one preferred embodiment, the opto-mechanical attachment may be formed using additive manufacturing techniques (e.g., 3D printing) although the invention is not so limited. The opto-mechanical attachment 12 forms a housing 18 that has an interior portion that contains one or more light sources 20 that are used to illuminate a sensing membrane 70 which is described herein for obtaining image(s) of the same. The one or more light sources 20 may include light emitting diodes (LEDs), laser diodes, or the like. The one or more light sources 20 are driven using driving circuitry 22 and powered by a power source 24 which may include one or more batteries. Alternatively, the power source 24 may be located external to the opto-mechanical attachment 12 and powered via a cord or the like (e.g., USB cord, power cord, or the like). A switch 26 located on the opto-mechanical attachment 12 may be used to turn the one or more light sources 20 on or off. In other embodiments, the switch 26 may be electronic and controlled using, for example, an application or app running on the portable electronic device 14.

As seen in FIGS. 1A and 1D, the housing 18 of the opto-mechanical attachment 12 includes a lens 28 mounted therein that lies along an optical path 30 along with the lens (not shown) of the portable electronic device 14 to enable an in-focus field of view for imaging the sensing membrane 70. FIG. 1D illustrates the optical patch 30 formed between the sensing membrane 70 and camera 16 of the portable electronic device 14. The camera 16 of the portable electronic device 14 includes an image sensor 32 (e.g., CMOS image sensors or the like) typically found in these types of devices for capturing images. The housing 18 may also include one or more processors 34 (e.g., microcontroller) that are used in conjunction with driving circuitry 22 to control operations of the portable reader device 10. In some embodiments, the one or more processors 34 may also perform various image processing and/or analysis functions described in more detail herein. This may include, for example, image processing of the images 80 obtained from the camera 16 of the portable electronic device or even generating or outputting the results of the test (e.g., thresholding or operating the trained deep neural network).

The portable reader device 10 is configured to receive a portion of a multi-part cassette 40 that includes the vertical flow assay components. In particular, one or more cassettes 40 are used for the multiplexed immunodiagnostic assay. With reference to FIG. 1B, the cassette 40 includes a first top or upper portion 42 that is detachably connected to a bottom or lower portion 44. The first top or upper portion 42 may include one or more posts, detents, or bosses 46 that interface with a slot or recess 48 contained in the bottom or lower portion 44 of the cassette 40. In this way, the first top or upper portion 42 of the one or more cassettes 40 are each detachably connected to the lower portion 44 by twisting the upper portion 42 onto the lower or bottom portion 44 (FIG. 1E). As seen in FIG. 1B, a second top or upper portion 50 is provided as part of the cassette 40. The second top or upper portion 50 also includes one or more posts, detents, or bosses 46 that interface with a slot or recess 48 contained in the bottom or lower portion 44 of the cassette 40. Both the first top or upper portion 42 and the second top or upper portion 50 are used together with the bottom or lower portion 44 and makeup a single cassette 40. The first top or upper portion 42 receives the sample (and buffers or other reagents) and the second top or upper portion 50 receives a buffer solution or other reagents/washes and serves as a signal generator by releasing antibody-conjugated nanoparticles 66 (see e.g., FIG. 3) as explained herein.

Figure 2:
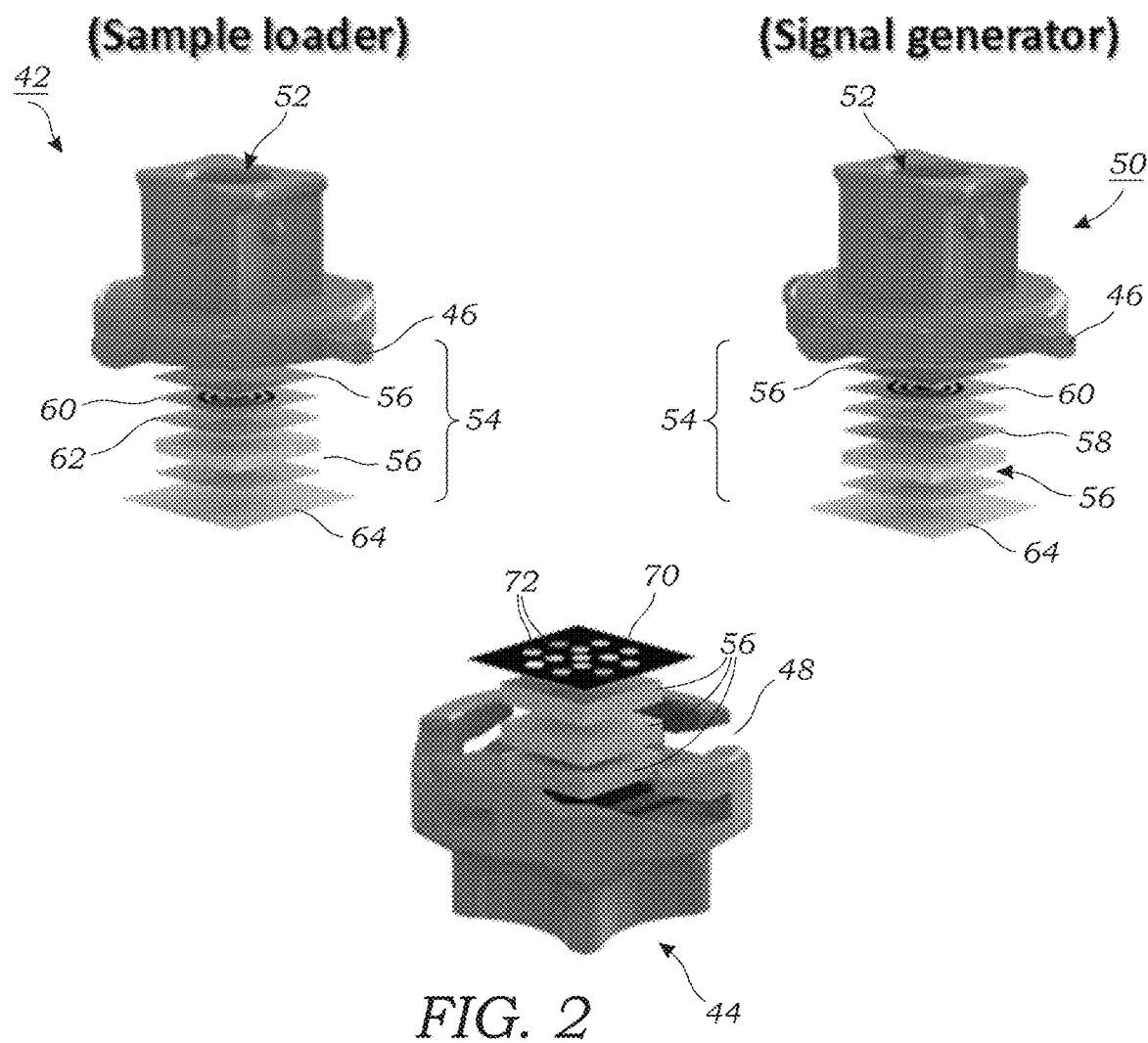
FIG. 2 illustrates perspective views of a single cassette that includes the bottom or lower portion and two (2) separate upper or top portions. The various discrete porous layers contained in each cassette section or portion is also illustrated. The first upper portion of the cassette receives the sample fluid via an aperture or hole and includes several porous layers including, in one embodiment, at least one absorption layer, one or more vertical flow layers, one or more spreading layers, a sample pad layer, and at least one supporting layer. The second upper portion of the cassette receives the buffer or other assay reagent fluid(s) or solution(s) and contains at least one absorption layer, one or more vertical diffusion layers, one or more spreading layers, at least one conjugation pad layer holding the antibody-conjugated nanoparticles therein, at least one sample pad layer, and at least one supporting layer.

FIG. 2 illustrates the vertical flow assay components contained in the first top or upper portion 42, the second top or upper portion 50, and the lower or bottom portion 44 of the cassette 40. The first top or upper portion 42 and the second top or upper portion 50 include an inlet 52 into which sample or other fluids (reagents, buffers, washes) are added for the vertical flow assay. A small volume of fluid (e.g., less than a few or several mL) is loaded into the inlet 52. The first top or upper portion 42 as well as the second top or upper portion 50 each includes a stack of discrete porous layers 54 which are described in detail below. Some of the discrete porous layers are used to absorb (e.g., absorption layers 56) fluid while other layers are designed to aid in fluid flowing particular directions. Other layers (such conjugation pad layer 58 in the second top or upper portion 50) contain reagents that are released in response to exposure to a fluid (e.g., antibody-conjugated nanoparticles 66). Some layers such as vertical flow diffuser layers 60 promote vertical (e.g., top-to-bottom) movement of fluid through the layer and inhibit lateral flow. Other layers such as spreading layers 62 promote lateral (e.g., horizontal) flow of fluid through the particular layer. Still other layers act as supporting structures (e.g., support layers 64). Preferably, the first top or upper portion 42 as well as the second top or upper portion 50 each contain at least one vertical flow diffuser layer 60 as described herein. FIG. 2 illustrates a single vertical flow diffuser layer 60 within the stack of porous layers 54.

Still referring to FIG. 2, the lower or bottom portion 44 of the cassette 40 holds a sensing membrane 70 with a plurality of spatially multiplexed immunoreaction spots or locations 72 formed therein. Each of the plurality of spatially multiplexed immunoreaction spots or locations 72 are disease-specific antigens and/or antibodies. In this regard, the antigens and/or antibodies are biomarkers for a particular condition or disease state. As explained herein, for Lyme disease, the plurality of spatially multiplexed immunoreaction spots or locations 72 may include one or more of Lyme disease antigens including OspC, BmpA, P35, P41, DbpB, Crsasp1, ErpD, Mod-C6, and anti-Human IgG/IgM. Different numbers of spots or locations 72 may be used depending on the assay but is typically more than three and less than twenty-five spots. Some of the spots or locations 72 may be used for positive (+) or negative (−) controls. Still other spots or locations 72 may also be used as fiducial marks to that can be used to register before and after images of the sensing membrane 70. The spots or locations 72 that are formed on the sensing membrane 70 may be defined on a nitrocellulose membrane (e.g., 0.22 μm pore size) by a black wax-printed (or other hydrophobic material) barrier, where each spot or location 72 is pre-loaded with a different capture-antigen or antigen epitope-containing peptide as well as proteins/antigens serving as positive-control and negative-control to enable multiplexed sensing information within a single test. The spatially isolated immunoreaction spots or locations 72 are defined by wax printed barriers, allowing for different capture antigens to be spotted on the nitrocellulose sensing membrane 70. For example, after printing, the sensing membrane 70 is incubated for 30 seconds at 120° C. in an oven to allow the printed wax to melt and diffuse downward into the nitro-cellulose. Each of the plurality of sensing spots 72 is then loaded with 1 μL of capture-antigen solution, and allowed to dry for 30 minutes at room temperature. Then, the sensing membrane 70 is dipped in 1% BSA in PBS solution for 30 minutes to block non-specific binding, and the sensing membranes 70 are again dried for 10 minutes at 37° C. in a dry oven. As seen in FIG. 2, one or more adsorption layers 56 (e.g., a thick pad if formed from multiple layers) is located beneath the sensing membrane 70 in the lower or bottom portion 44 of the cassette 40.

To perform the assay with the multiplexed immunodiagnostic assay device 2 a user sample is collected. The user sample may include, for example, a small (less than 1 mL) serum sample obtained from a human mammal. The sample is then processed through the cassette 40 formed with the first top or upper portion 42 secured to the lower or bottom portion 44. First, a small volume (e.g., 200 μL) of buffer is placed into the inlet 52. Gravity and the natural wicking motion move the fluid through the stack of porous layers 54. This operation may take several seconds (e.g., 20 seconds). Next, a small volume of the serum sample (e.g., 20 μL although it may be more or less) is placed into the inlet 52. This operation may take several seconds (e.g., 10 seconds). Another small volume (e.g., 200 μL) of buffer is placed into the inlet 52. The cassette 40 is then allowed to incubate for several minutes (e.g., 6 minutes). After incubation, the first top or upper portion 42 is removed from the lower or bottom portion 44. The second top or upper portion 50 is then secured to the lower or bottom portion 44 of the cassette 40 that was just used in the prior sequence of operations. Next, a volume (e.g., 450 μL) of buffer is placed into the inlet 52 which then flows through the stack of porous layers 54 including the conjugation pad 58 which releases the antibody-conjugated nanoparticles 66. The antibody-conjugated nanoparticles 66 then bind with the corresponding spots or locations 72 of the sensing membrane 70 (or flow through the sensing membrane 70 if no binding occurs). The cassette 40 may be allowed to incubate for a certain period of time (e.g., several minutes) to allow for binding of the antibody-conjugated nanoparticles 66. In addition, a wash solution may be loaded into the inlet 52 to wash away non-bound antibody-conjugated nanoparticles 66. The antibody-conjugated nanoparticles 66 may include embedded gold nanoparticles (AuNPs) that are conjugated to anti-human IgM or IgG antibodies (or other antibodies).

Gold nanoparticle (AuNP)-antibody conjugates may be synthesized by adding 900 μL of gold nanoparticle solution (1 OD), 100 μL 0.1M borate buffer (pH 8.5) and 10 μL of the antibody (1 mg/mL) to a sterile Eppendorf. The materials are incubated for 1 hour at room temperature, then 100 μL BSA (1% in PBS) is added and incubated for 30 minutes at room temperature, acting as a blocking protein to prevent non-specific binding. The AuNP conjugates are centrifuged at 4° C. for 15 min at 8000 rpm, and then washed with 1 mL 10 mM Tris buffer (pH 7.4) three times. After the final wash, 100 µL of storage buffer (0.1 M pH 8.5 borate buffers with 0.1% BSA and 1% sucrose) is added to the supernatant, and the final concentration of AuNP antibody conjugate can be confirmed by optical density measurement at 525 nm. A small aliquot such as 70 µL of the 2 OD conjugate solution is then pipetted onto each conjugation pad 58 (1.2×1.2 cm) for loading, and the conjugation pads 58 are dried at 37° C. for 1 hour.

The antibody-conjugated nanoparticles 66 then bind to the disease-specific IgM or IgG antibodies previously captured on the sensing membrane 70, resulting in a color signal in response to the captured amount. This color signal response is captured in images obtained using the portable reader device 10. Specifically, after incubation and washing of the cassette 40, the second top or upper portion 50 is removed from the lower or bottom portion 44 of the cassette 40 and the lower or bottom portion 44 of the cassette 40 is then inserted into the portable reader device 2 as illustrated in FIG. 1A. The housing 18 may include a similar post, detent, or boss 46 that interfaces with the slot or recess 48 on the lower or bottom portion 44 of the cassette 40 using a similar twisting engagement/disengagement.

FIG. 1C illustrates a screen or display 17 of a portable electronic device 14 showing an obtained image of the sensing membrane 70. Each individual spot or location 72 on the sensing membrane 70 will have a particular color signal response that can then be quantified and used to automatically generate a diagnosis (e.g., positive (+) or negative (−)) for the input sample. In other embodiments, in addition or separate from a diagnosis, the device 2 may also output a concentration of one or more biomarkers. The portable electronic device 14 may include an application or "app" that is executed on the portable electronic device 14 that includes a graphical user interface (GUI) that can be used to run the assay or test and display results therefrom. For example, the GUI may display an image of the sensing membrane 70 (either raw or after image processing) as well as the quantified intensity values of the spots or locations 72. The GUI may also display one or more of: patient ID, test location, test time, test type (e.g., Lyme disease), diagnosis (e.g., positive (+), negative (−), biomarker concentration, cassette ID, and the like.

Figure 3:
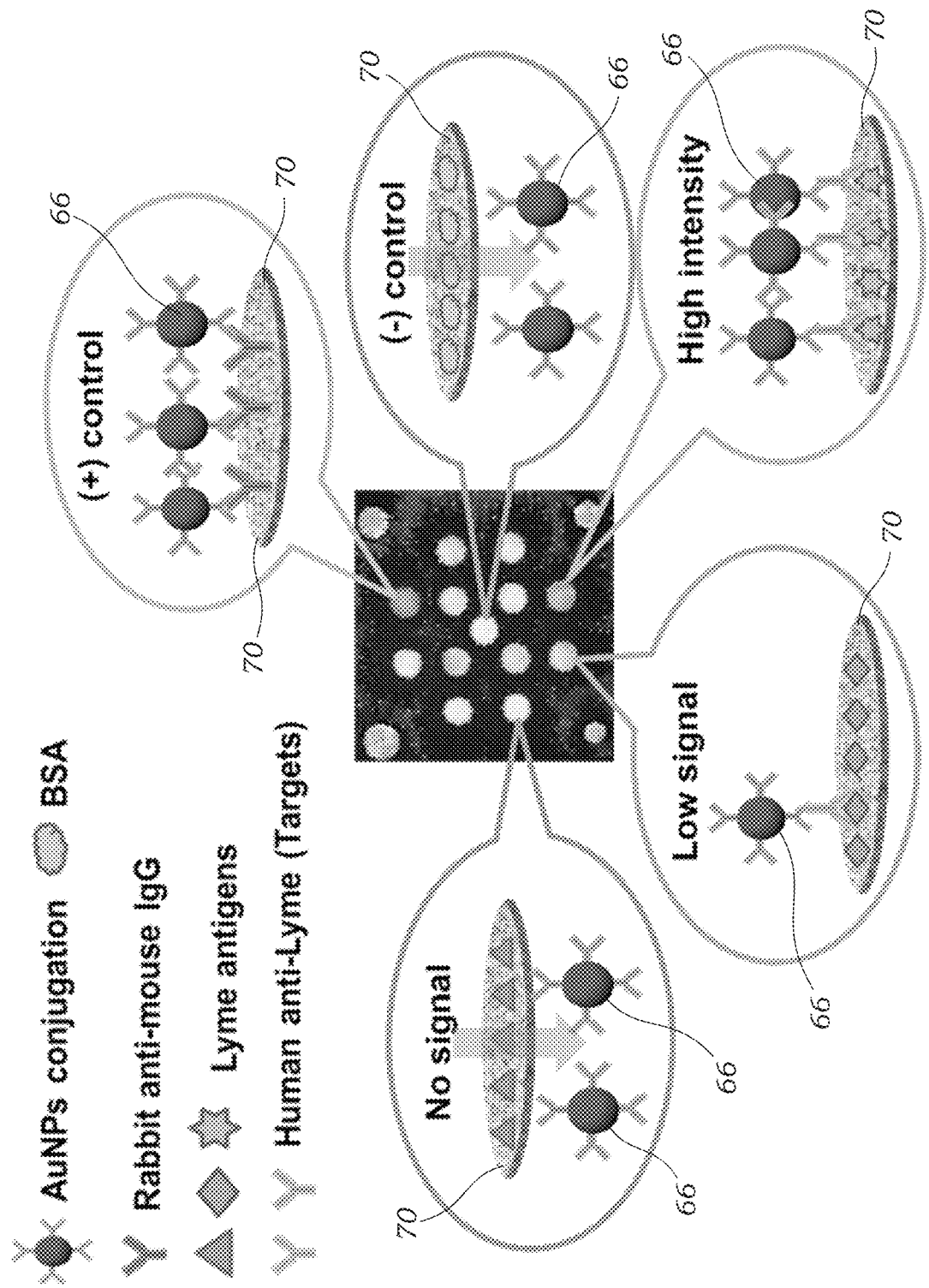
FIG. 3 illustrates the nature of the multiplexed immunoreactions which occur on the sensing membrane during the assay operation. In this example, Lyme disease antigens are located in the spots or locations on the sensing membrane. No signal, low signal, and high intensity (or high signal) spots are illustrated along with a positive (+) control and negative control (−).

FIG. 3 illustrates the nature of the multiplexed immunoreactions which occur on the sensing membrane 70 during the assay operation. A sensing membrane 70 includes spatially discrete spots or locations 72 formed with disease-specific antigens and/or antibodies. In this specific embodiment, the spots or locations 72 Lyme disease-specific antigens. One or more of the spots or locations 72 is a positive (+) control and one or more spots or locations 72 is a negative (−) control. Some spots or locations 72 may have no color signal response (no signal in FIG. 3) because the antibody-conjugated nanoparticles 66 do not bind to the spots or locations 72. Other spots or locations 72 may have a low color signal response (e.g., low signal in FIG. 3) because few antibody-conjugated nanoparticles 66 bind to the spot or location 72. Still other spots or locations 72 may have a high color signal response (e.g., high intensity in FIG. 3) because many antibody-conjugated nanoparticles 66 bind to the spot or location 72. The negative control spot or location 72 does not bind to the antibody-conjugated nanoparticles 66 as the spots or locations 72 are all bound with BSA which prevents the antibody-conjugated nanoparticles 66 from binding thereto. Conversely, the positive control spot or location 72, in this embodiment, has bound rabbit anti-mouse IgG.

Figure 15A:
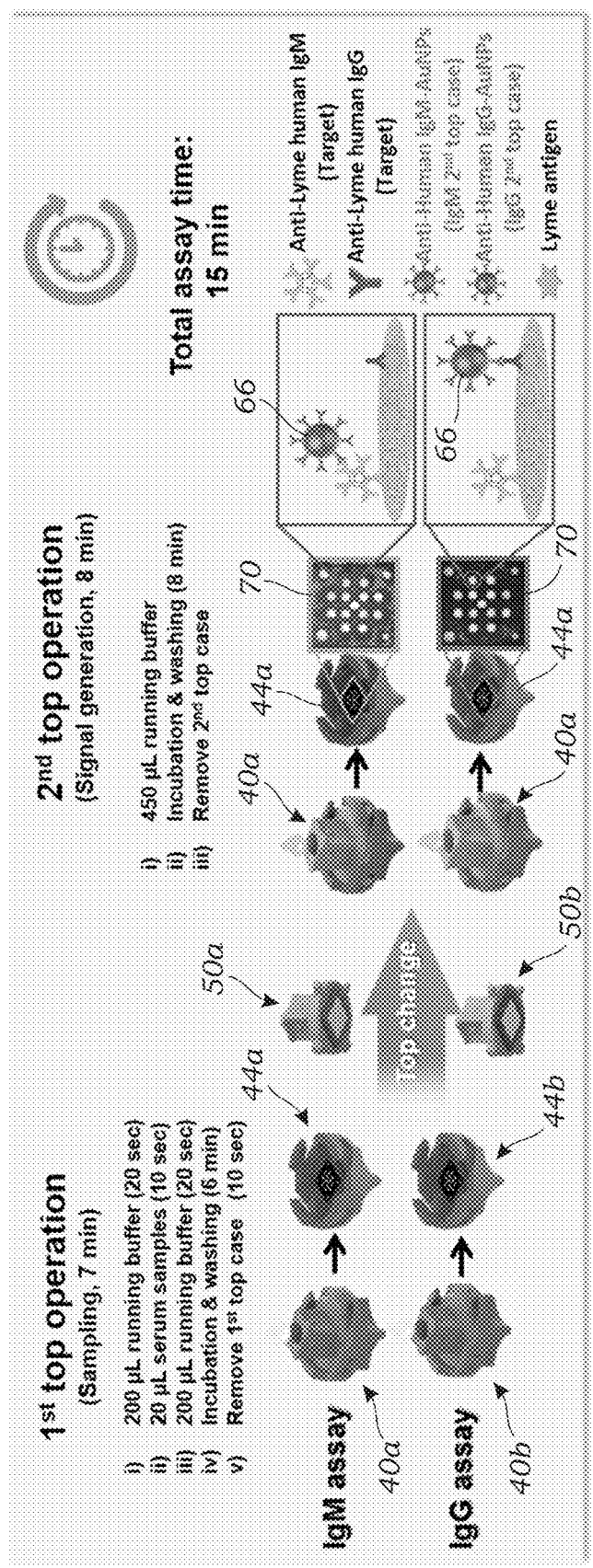
FIG. 15A illustrates the xVFA sequence of operations for the IgM and IgG assays, which are performed in parallel (total assay time: 15 min). A schematic depiction of the IgM and IgG immunoassays is shown to the right.

In some embodiments, the multiplexed immunodiagnostic assay device 2 may use multiple sets of cassettes 40 for the assay (e.g., cassettes 40a, 40b in FIG. 15A). For example, for Lyme disease two separate assays may be performed in parallel with patient or subject sample with one cassette 40a being used for an IgM assay and another cassette 40b being used for an IgG assay. For the IgM assay, a first cassette 40a is provided that includes, along with the lower or bottom portion 44, a first top or upper portion 42a and a second top or upper portion 50a that includes a conjugation pad 58 that contains anti-human IgM-AuNPs. For the IgG assay, a first cassette 40b is provided that includes that includes, along with the lower or bottom portion 44, a first top or upper portion 42b and a second top or upper portion 50b that includes a conjugation pad 58 that contains anti-human IgG-AuNPs. The bottom portions 44 for both cassettes 40a, 40b contains the same sensing membrane 70 with spots or locations 72. An example of this type of assay is illustrated in FIG. 15A. In this embodiment, the portable reader device 2 images both bottom portions 44 of the cassettes 40a, 40b prior to outputting a diagnosis or biomarker concentration.

Figure 4A:
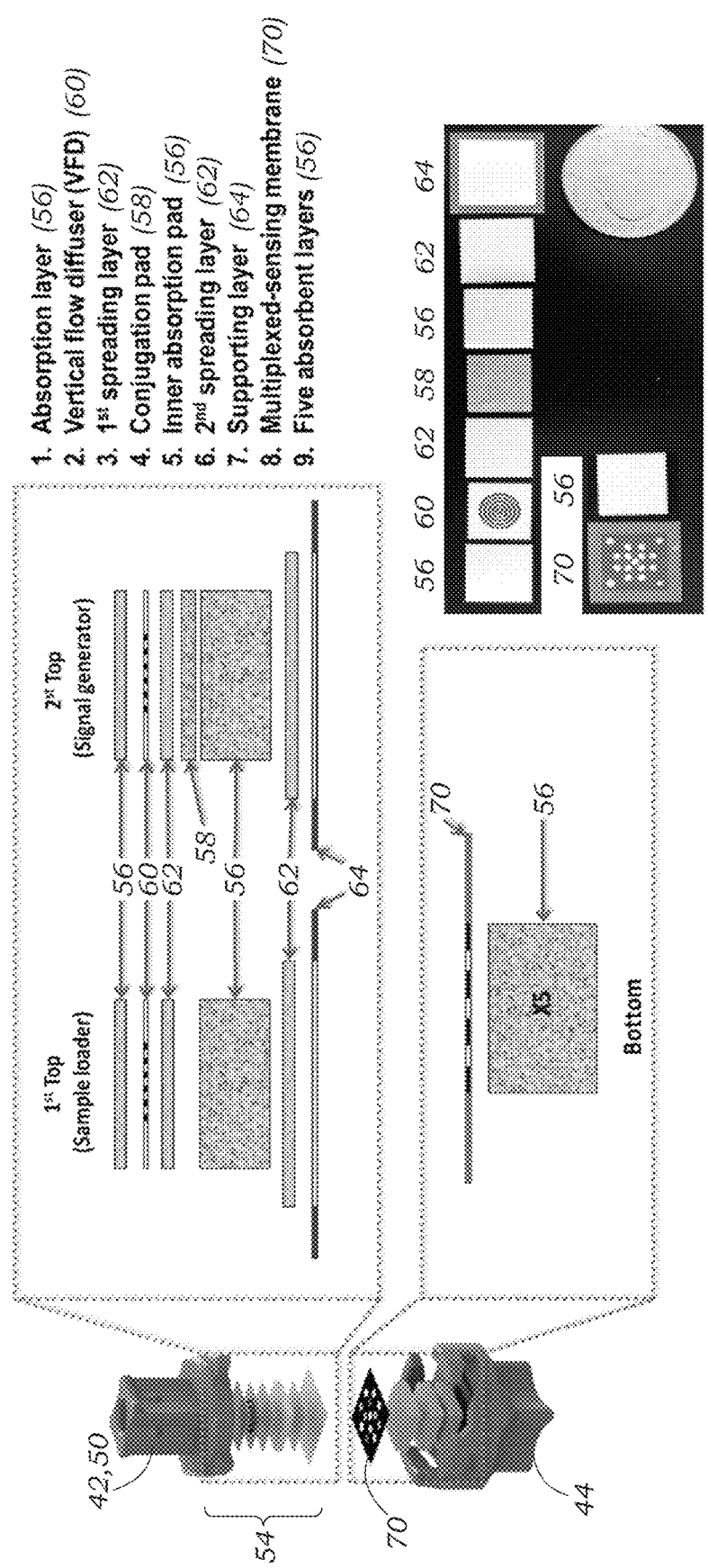
FIG. 4A illustrates an exploded diagram view of the multiplexed vertical flow assay detailing the different porous layers contained within the 3D-printed cassette (right image). A quarter is show in the bottom right image for scale.

FIG. 4A illustrates an exemplary construction of stack of porous layers 54 of the first and second top or upper portions 42, 50 and the bottom or lower portion 44 of the cassette 40. In this embodiment, for the first top or upper portion 42, the top layer includes an absorption layer 56 followed by a vertical flow diffuser layer 60. A first spreading layer 62 is located beneath the vertical flow diffuser layer 60 followed by an adsorption layer or pad 56. A second spreading layer 62 is located beneath adsorption layer or pad 56. A supporting layer 64 (e.g., 0.22 µm nitrocellulose membrane) is located as the bottom-most layer of the stack of porous layers 54. The second top or upper portion 50 includes, for the top layer, an absorption layer 56 followed by a vertical flow diffuser layer 60. A first spreading layer 62 is located beneath the vertical flow diffuser layer 60 followed by a conjugation pad 58. An adsorption layer or pad 56 is located beneath the conjugation pad 58. A second spreading layer 62 is located beneath adsorption layer or pad 56. A supporting layer 64 is located as the bottom-most layer of the stack of porous layers 54. The bottom or lower portion 44 of the cassette 40 includes the sensing membrane 70 along with multiple (e.g., five) absorption layers 56. FIG. 4A also illustrates an image of the various membranes.

Figure 4B:
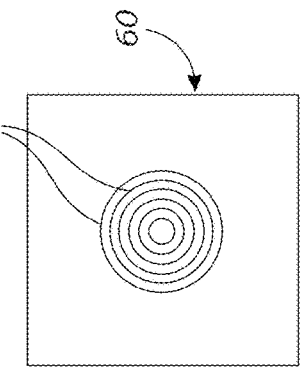
FIG. 4B illustrates a vertical flow diffuser layer that includes a plurality of concentric rings or circles formed on or in a porous substrate.
Figure 5A:
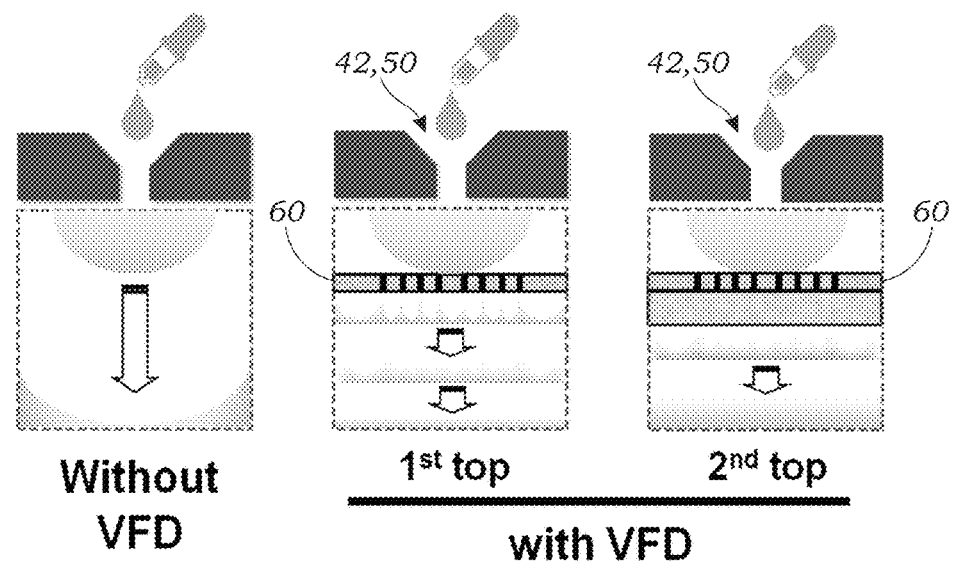
FIG. 5A illustrates a schematic illustration of a cassette demonstrating improvement of vertical flow uniformity by use of the vertical flow diffusion layer.
Figure 5B:
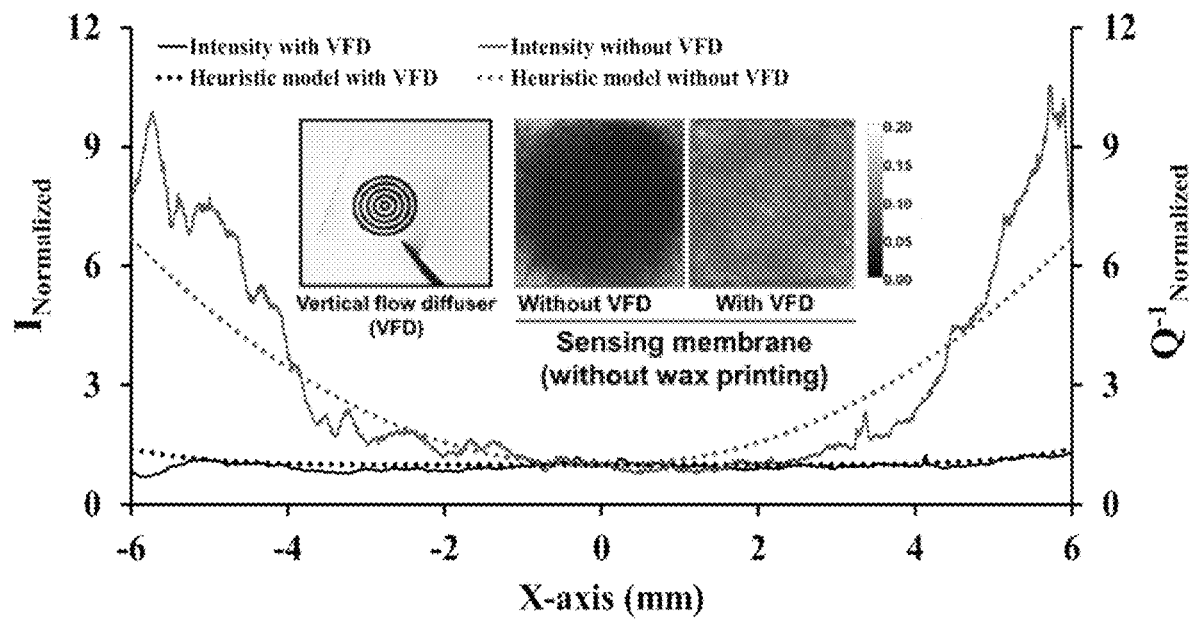
FIG. 5B illustrates a graph of signal intensity distribution of with/without VFD at the no wax printed sensing membrane and comparison with the simulation of three-dimensional vertical flow rate distribution along the x-axis using Darcy's law (insert: image of vertical flow diffuser and no wax printed sensing membranes). The rabbit anti-OspC antibody was immobilized on the sensing membrane and anti-rabbit IgG conjugated gold nanoparticles were used for this model test.
Figure 5C:
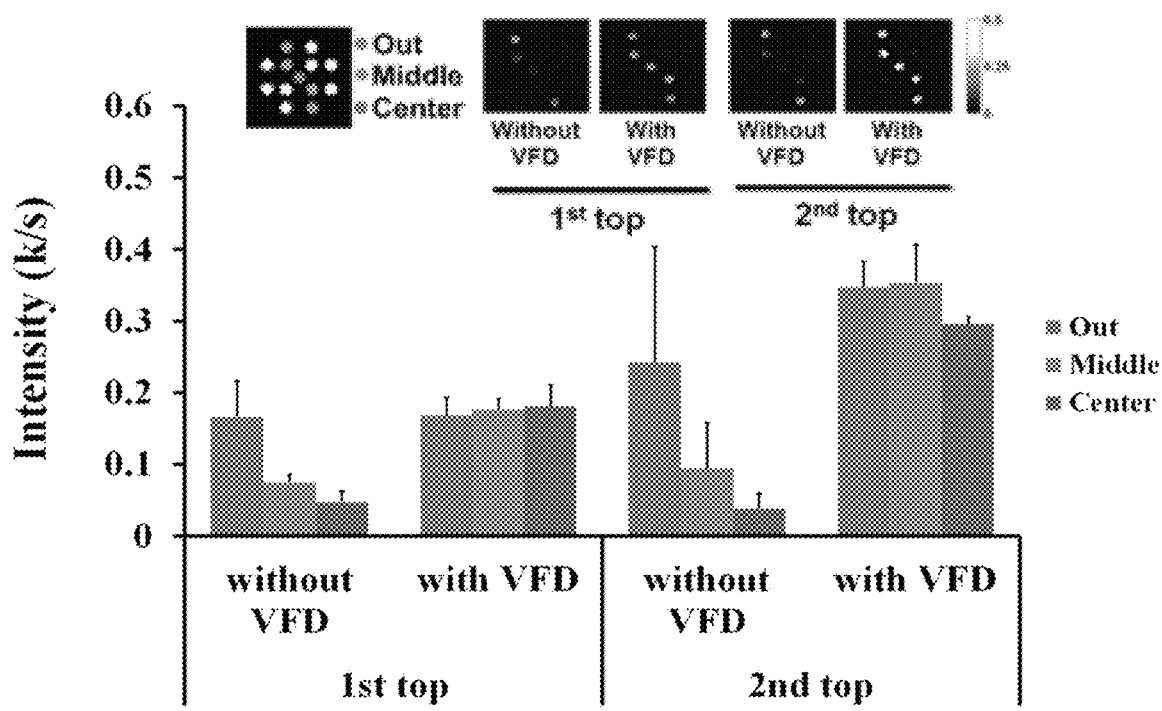
FIG. 5C illustrates histograms illustrating the comparison of signal intensity at the wax printed multiplexed sensing membrane by spot positions (out, middle, center) of multiplex sensors with reference to the presence of a vertical flow diffusion layer and without the vertical flow diffusion layer (insert: k/s intensity images).

The porous layers 54 may be made of a number of different materials including, porous paper, glass fiber, cotton, and/or polymer layers. The vertical flow diffuser layer 60 may be made from a nitrocellulose (NC) membrane (e.g., 0.45 µm pore size) that is wax printed with a plurality of concentric barriers (rings or circles) of varying sizes as seen in FIGS. 4A and 4B (showing wax printed circles on NC membrane). Flow uniformity laterally across the sensing membrane 70 is critical for the assay as it relies on spatial multiplexing. Darcy's law states that in porous media, volumetric flow-rate is inverse to flow distance, meaning that the larger the cross-sectional area of the multiplexed vertical flow assay, the more non-uniform the flow will be as the flow has to both spread laterally and vertically at the edges of the device. This poses clear drawbacks in terms of assay performance and illustrates a trade-off between functional multiplexing area and signal uniformity. The wax printed vertical flow diffuser layer 60 (VFD) addresses this challenge. When the loaded samples and solution contact the wax barriers, multiple concentric flows emanate from the vertical flow diffuser layer 60, culminating in an even distribution of flow rates across the sensing membrane 70. Without the vertical flow diffuser layer 60, center-to-edge flow emanating from the loading inlet results in non-uniform volumetric flow-rates across the sensing membrane. This is illustrated schematically in FIG. 5A. FIG. 5B illustrates the signal intensity distribution across the surface of a sensing membrane 70 with and without VFD and a comparison with the simulation of three-dimensional vertical flow rate distribution along the x-axis using Darcy's law (insert: image of vertical flow diffuser layer and sensing membrane (without wax printing). The rabbit anti-OspC antibody was immobilized on the sensing membrane 70 and anti-rabbit IgG conjugated gold nanoparticles 66 were used for this model test. FIG. 5C illustrates a comparison of signal intensity (k/s intensity as described herein) at a wax printed multiplexed sensing membrane 70 by spot 72 positions (out, middle, center) of multiplex sensors with reference to the presence of a VFD (insert: k/s intensity images).

When the vertical flow diffuser layer 60 is absent, a large vertical flow intensity variation (nearly 1000%) between the center and the outside spots is observed (FIG. 5B), as the colorimetric signal generated during the assay is inversely proportional to the volumetric vertical flow rate of the sample. Therefore, in the presence of the vertical flow diffuser layer 60, the % coefficient of variation (CV, the ratio of the standard deviation to the mean of signal intensity) of signal intensity decreases from 94% to 12.9% across all active spots (FIG. 5C). For the vertical flow diffuser layer 60, the number of concentric wax circles or rings that are formed on the porous substrate (e.g., nitrocellulose) may vary but is typically two or more and less than ten. For example, a typical vertical flow diffuser layer 60 may have between 4-6 wax circles or rings. FIG. 4B illustrates a vertical flow diffuser layer 60 with five (5) discrete rings or circles 61 of wax (or other water barrier material) formed on a nitrocellulose substrate.

Some of the discrete layers of the stack of porous layers 54 may be made from asymmetric membranes with varying pore sizes in the vertical or z-direction. For example, the top absorption layer 56 in the first and second top or upper portions 42, 50 may be made from an asymmetric membrane with larger pores (e.g., around 550 μm$^2$) facing upward and the smaller pores (e.g., around 5 μm$^2$) facing downward. Likewise, the spreading layers 62 may also be formed from asymmetric membranes with varying pore sizes in the vertical or z-direction, however, the side of the membrane with the larger pores faces the downward direction. When the small pore side contacts the upper layer, the sample flows laterally before it can flow out of the large pore size due to reverse capillary action. This lateral spreading flow reduces the vertical flow non-uniformity and non-repeatability as well as increases the overall signal intensity by slowing down the vertical flow rate to allow more time for binding of analyte and antibody-conjugated nanoparticles 66 to the sensing membrane 70.

Figure 6:
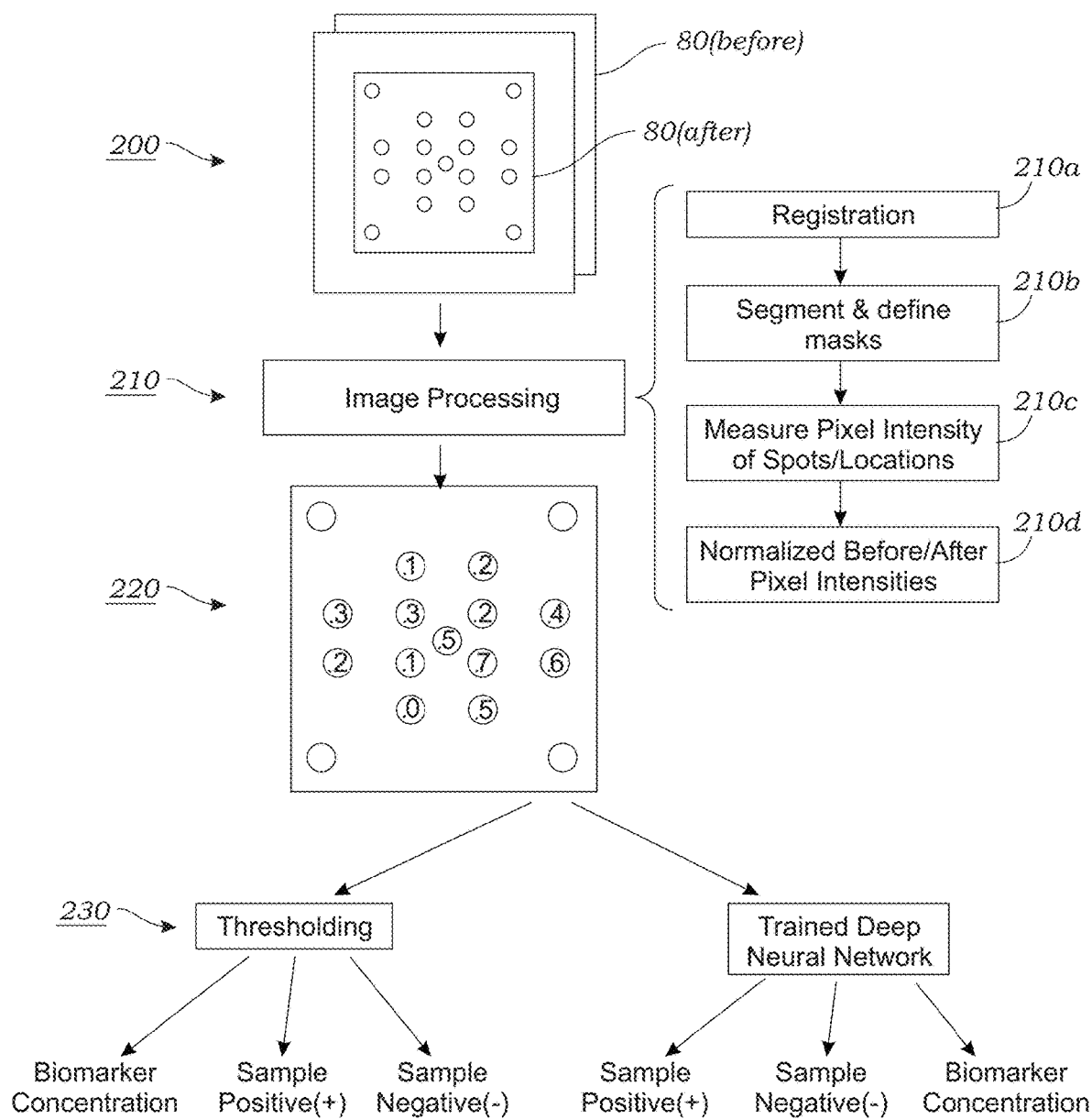
FIG. 6 illustrates a general sequence of operations that are performed by the multiplexed immunodiagnostic assay device after image(s) are obtained of the sensing membrane using the portable reader device according to different embodiments.
Figure 7:
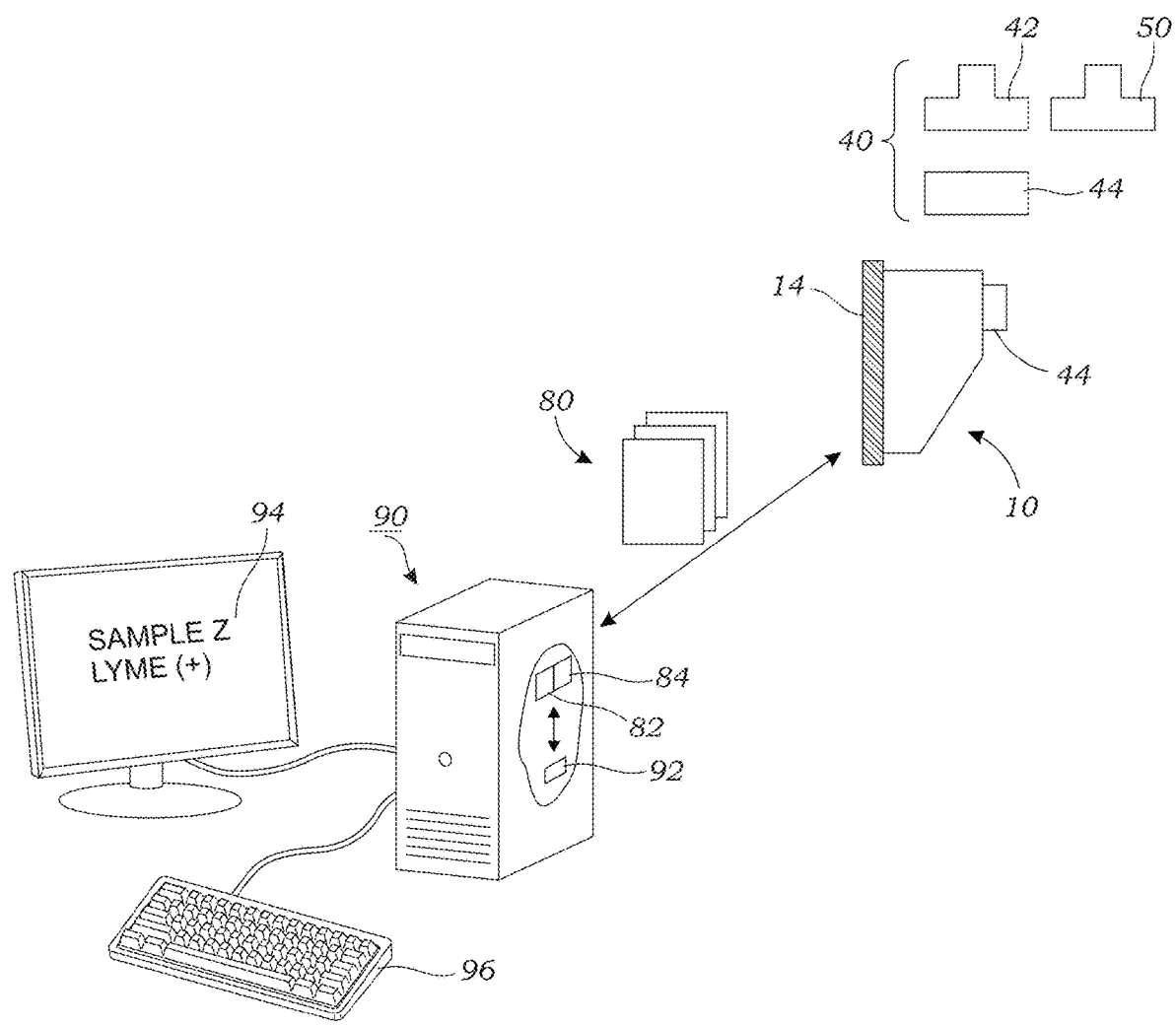
FIG. 7 illustrates one embodiment of a system that includes the multiplexed immunodiagnostic assay device.

FIG. 6 illustrates a general sequence of operations that are performed by the multiplexed immunodiagnostic assay device 2 after image(s) 80 are obtained of the sensing membrane 70 using the portable reader device 10 (operation 200 in FIG. 6). FIG. 6 illustrates two such images 80 with one image 80 being a "before" image 80 of the sensing membrane 70 prior to introduction of the sample and assay and reagents and an 'after' image 80 of the sensing membrane 70 the assay described herein has been performed. The before image 80 is acquired by imaging the membrane 70 in the bottom/lower cassette portion 44 prior to running the assay. Next, in operation 210, the images 80 to image processing operations using image processing software 82 (FIG. 7). The image processing software 82 may extract a single color from a multi-color image (e.g., green) and registers (operation 210a) the before and after images 80 and segments the regions of the images 80 that correspond to the spots or locations 72 and defines a mask (e.g., circle of particular radius) for each spot or location 72 (operation 210b). The image processing software 82 measures the pixel intensity for the masked region corresponding to each spot or location 72 (operation 210c). The pixel intensity may include a mean, average, k/s statistic, or other statistical measure for each spot or location 72. The pixel intensity may include a monochrome intensity value or a color intensity value. Finally, the image processing software 80 normalizes the before/after pixel intensities as seen in operation 210d.

Normalized pixel intensity values are then assigned to each spot or location 72 as illustrated in operation 220 of FIG. 6. For example, the normalized pixel intensity value may include a number corresponding to normalized pixel intensity (pixel intensity values after the assay are normalized to the pixel intensity of the blank membrane 70 before the assay). In this particular illustration, normalized pixel intensity values between 0 and 1 are assigned to each spot or location 72 but it should be appreciated that other numerical ranges may be employed. In addition, as explained herein, each spot or location 72 may be assigned a k/s statistical value in some embodiments. Next, analysis software 84 is used to automatically generate one or more outputs based at least in part of the normalized pixel intensity values associated with each spot or location 72 as seen in operation 230. In one embodiment, the analysis software 84 uses thresholding of normalized pixel intensity values of one or more of the spots or location 72 to generate a positive (+) or negative (−) diagnosis for the sample that is tested. For example, if particular spots or locations 72 have normalized pixel intensity values that exceed certain established thresholds which are empirically derived based on known positive samples, then the tested sample may be deemed positive (+). Conversely, if the normalized pixel intensity values do not established thresholds, then the tested sample may be deemed negative (−). The thresholding may include combinations of spots or location 72. The thresholding may also be used to output an inferred concentration or concentration range of one or more biomarkers contained in the sample. In some embodiments, raw after pixel intensity values may be used instead of normalized pixel intensity values.

In another embodiment, the analysis software 84 uses a trained deep neural network that receives as an input the normalized pixel intensity values generated by the image processing operation 210 and automatically outputs or generates a diagnosis for the sample. As explained herein, the $R_m$ signals obtained from the images 80 of the plurality of immunoreaction spots or locations 72 are input to a trained decision neural network executed by the analysis software 84. The trained neural network of the analysis software 84 may output a network output having a numerical value between 0 and 1 which reflects a confidence score. Of course, other ranges may be used for the confidence score including non-numerical ranges. A binary diagnosis is then made based on comparison with a cutoff value. For example, positive (+) samples may be those with numerical outputs or confidence scores from the trained decision neural network that exceed the cutoff (e.g., 0.5). Conversion, negative (−)

samples may be those with numerical outputs from the trained decision neural network that are below the cutoff. In this regard, the sample may be indicated as positive (+) or negative (+) by the trained deep neural network. Alternatively, or in addition to indicating that the sample is positive (+) or negative (+), the trained deep neural network executed by the analysis software 84 may also output a concentration or concentration range of one or more biomarkers contained in the sample. The response of the trained deep neural network is quick outputting a result within a few seconds or even less than a second.

FIG. 7 illustrates one embodiment of a system 4 that includes the multiplexed immunodiagnostic assay device 2. In this embodiment, the system 4 includes a computing device 90 having one or more processors 92 that are used to execute the image processing software 82 and analysis software 84 described herein. It should be appreciated that image processing software 82 and analysis software 84 may not be separate programs or applications but may be integrated into a single program or application. The computing device 90 may include either a local computing device 90 that is co-located with the portable reader device 10 and connected via a wired or wireless connection (e.g., using Bluetooth or other near-field communication protocol) or it may be a remotely located computing device 90 and connected via a wide area network such as the Internet. The computing device 90 may include a personal computer, laptop, tablet PC, one or more servers (for remote processing), and the like. It should also be appreciated that in other embodiments, the processor 34 of the portable reader device 10 or even a processor of the portable electronic device 14 may be used to perform tasks of the image processing software 82 and/or the analysis software 84.

FIG. 7 illustrates the portable reader device 10 that is used to obtain the images 80 of the sensing membrane 70 as described herein. The raw image files 80 themselves are transferred to the computing device 90 which then performs image processing and outputs the final diagnosis/result using the image processing software 82 and/or the analysis software 84. Alternatively, the computing device 90 may be integrated with the portable reader device 10 itself or with the portable electronic device 14 and used to perform image processing and outputting the final diagnosis/result. In the embodiment of FIG. 7, the computing device 90 further includes a display 94 and one or more input devices 96 which are used to view the results, image(s) 80, assay data, etc. The computing device 90 may also be used to transfer the assay test results and other assay or test data back to the portable reader device 10 and/or portable electronic device 14 in other embodiments. For example, the raw image files 80 may be transferred to the computing device 90 for image processing and analysis using image processing software 82 and/or the analysis software 84 and the results and other test data may be returned to the portable electronic device 14 (e.g., mobile phone) for display thereon.

Figure 8:
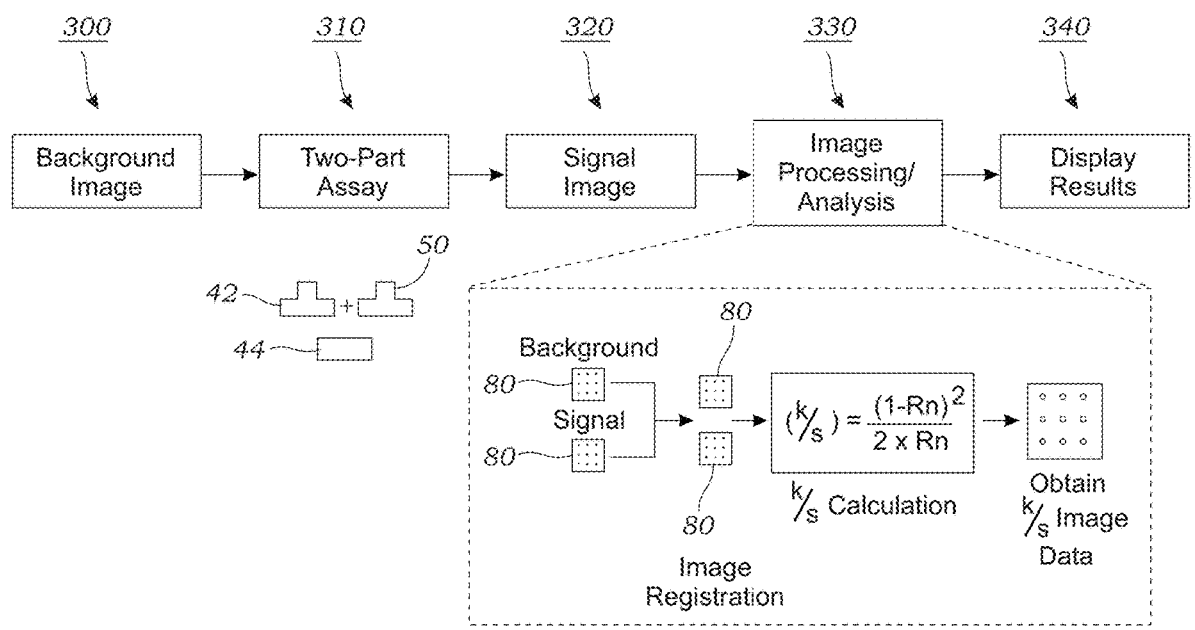
FIG. 8 illustrates a sequence of operations used to perform a test or assay with the multiplexed immunodiagnostic assay device that uses k/s values.

FIG. 8 illustrates a sequence of operations used to perform a test or assay with the multiplexed immunodiagnostic assay device that uses k/s values. In this embodiment, the test is started in operation 300 where the portable reader device 10 first takes a background image of the sensing membrane 70 prior to running the assay. Then, with reference to operation 310, the first top/upper cassette portion 42 and bottom/lower cassette portion 44 are assembled together, and 200 μL of running buffer (1.6% BSA and 3% tween 20 in PBS) is dispensed into the inlet 52. After 1 minute, 50 μL of the sample is dispensed into the inlet 52 of first top/upper cassette portion 42, followed by another 200 μL of running buffer one minute later. Then the fluids are allowed to flow through the stack of porous layers 54 for six (6) minutes, before the first top/upper cassette portion 42 is exchanged with the second top/upper cassette portion 50 containing the conjugation pad layer 58. An additional 400 μL of running buffer is dispensed into the inlet 52 of the second top/upper cassette portion 50 and allowed to flow for eight (8) minutes, marking the end of the sandwich immunoassay. The second top/upper cassette portion 50 is then removed and an image 80 of the sensing membrane 70 is again taken as seen in operation 320 with the portable reader device 10 (imaging takes place without the second top/upper cassette portion 50).

The images 80 may be in any number of formats including, for example, raw, .dng format using the standard camera application or app on the portable electronic device 14. The images 80 are then transferred to the computing device 90 (e.g., sent to a remote server 90) for processing and analysis as seen in operation 330. For example, image processing software 82 (e.g., MATLAB script or other language) converts the images 80 to tiff format and selects one of the color channels (e.g., the green channel in one particular embodiment). The background and signal images 80 are then registered, and the signal image is divided by the background image, and used to calculate the k/s statistic per pixel as defined by a special case of Kubelka-Munk theory where the reflection substrate is considered opaque (i.e. infinite thickness), $$(k/s)_n = \frac{(1 - R_n)^2}{2 \times R_n} \quad \text{Eq. 1}$$

where k is the absorption coefficient, s is the scattering coefficient of the layer, Rn is per pixel intensity ratio between the registered signal and background image 80, and n is the pixel index. The k/s image, along with the average k/s statistic per sensing spot or location 72 (k/s data) is calculated and then sent back to the custom smartphone application. The results are then displayed as seen in operation 340 in the graphical user interface (GUI) revealing to the user information regarding the sample which may include relative disease-specific antibody concentrations in the sample (e.g., Lyme disease), disease diagnosis (e.g., positive (+), negative (−), or the concentration/concentration range of one or more biomarkers.

Figure 9A:
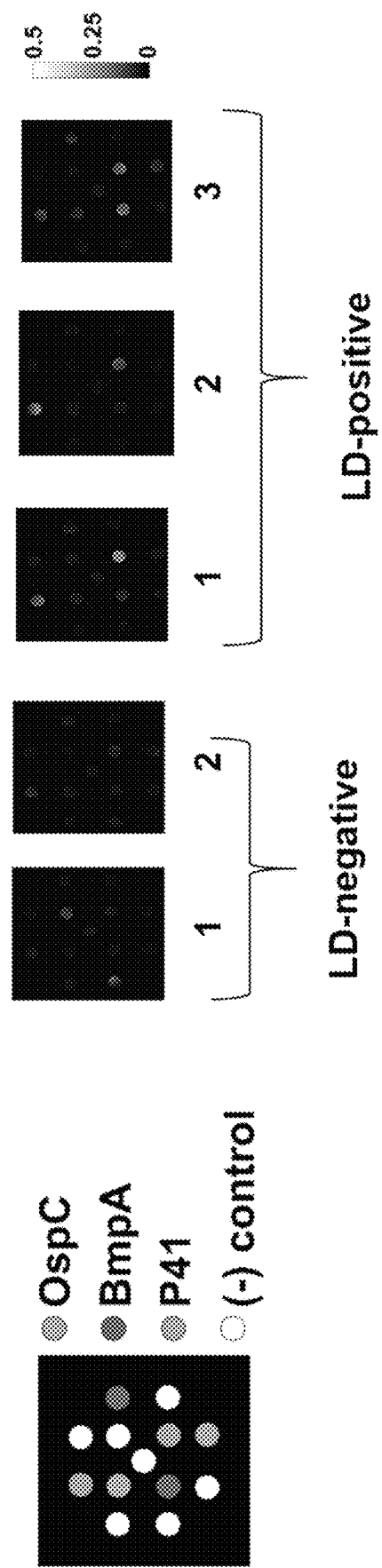
FIG. 9A illustrates the antibody spot legend (left) and k/s images using human samples for LD-negative and LD-positive samples.
Figure 9B:
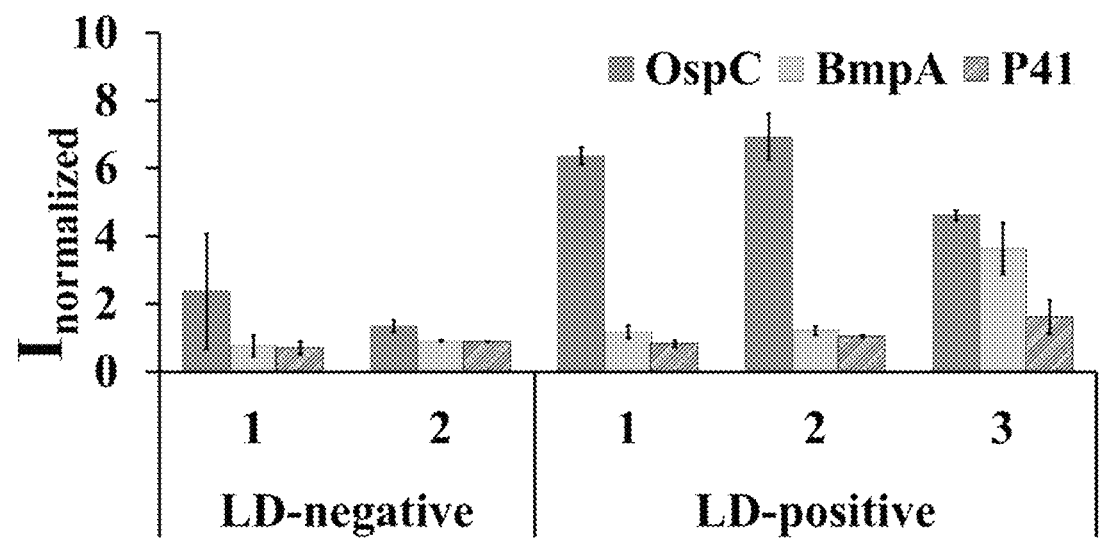
FIG. 9B illustrates an intensity plot from analyzed k/s images (n=2).
Figure 9C:
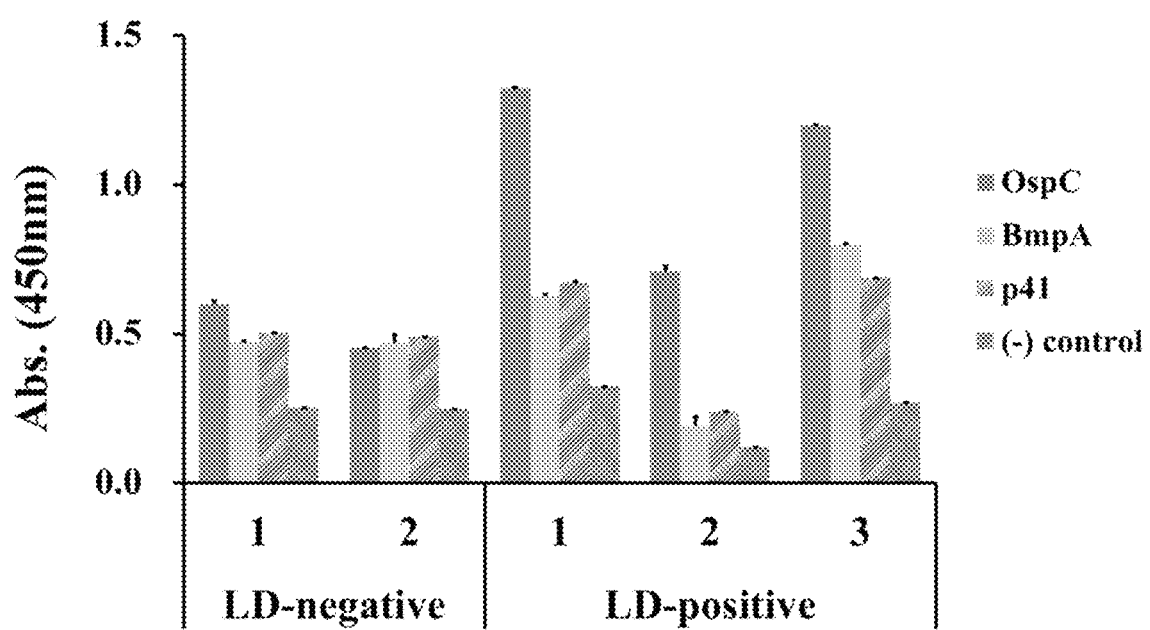
FIG. 9C illustrates ELISA results for the real human samples.

FIGS. 9A and 9B illustrate the ability of the multiplexed immunodiagnostic assay device 2 to distinguish Lyme-specific IgM-positive and negative human samples in order to verify its applicability to real POC diagnostics. In this test, OspC, BmpA, and P41, along with negative controls were used as antigens formed on the sensing membrane 70 and then imaged and subject to k/s image intensity analysis. As seen in FIG. 9B, a clear difference in signal intensity is seen between the negative and positive samples, and the results match closely with the ELISA results (FIG. 9C). Interestingly, a negative control signal in the ELISA test did not appear in the corresponding multiplexed vertical flow assay results. In the case of the Lyme positive-1 sample, a negative control level 24.3% of OspC signal can be seen in the ELISA test, compared to the 9.2% in the multiplexed immunodiagnostic assay device 2. This result demonstrates that the optimized two-part operation of the multiplexed immunodiagnostic assay device 2 works effectively for real human samples, showing potential as a multiplexed POC assay tool for diagnosing Lyme disease. While multiple antibody signals were above control levels for patient 3, including OspC, for Lyme positive-1 and 2 samples, only the signal of OspC was detected with about 3 to 4 times higher signal intensity than the negative samples, suggesting differences in the immune repertoire between patients.

For the ELISA tests, Lyme antigens (50 μL, 200 ng/mL) in pH 9.0 0.1M carbonate buffer were incubated for two hours in a 96 well-plate at room temperature. Wells were washed with PBST three times then incubated with 100 μL of 1% bovine serum albumin (BSA) in PBS for 2 hours at room temperature to prevent non-specific binding. After washing with PBST three times, 50 μL of the spiked anti-Lyme antibodies (anti-OspC, anti-BmpA and anti-P41) 1% BSA in PBS (1 μg/mL) and the plates were incubated for 2 hours at room temperature. Plates were washed with 100 μL PBST and 50 μL goat anti-rabbit IgG HRP conjugate (4000 times dilution in 1% BSA in PBST) was added to each well and incubated at room temperature for 30 minutes. The plate was washed with PBST (three times), D.I. water (3 times), and tetramethylbenzidine (TMB) was added to each well to react for 15 minutes. The reaction was stopped with 50 μL of 0.2M $H_2SO_4$ and absorbance was measured at 450 nm using a well plate reader (Synergy, BioTek®, Winooski, VT, USA). For the control human sample assay, the same assay was performed with the samples diluted 20 times in 1% BSA.

Figure 15B:
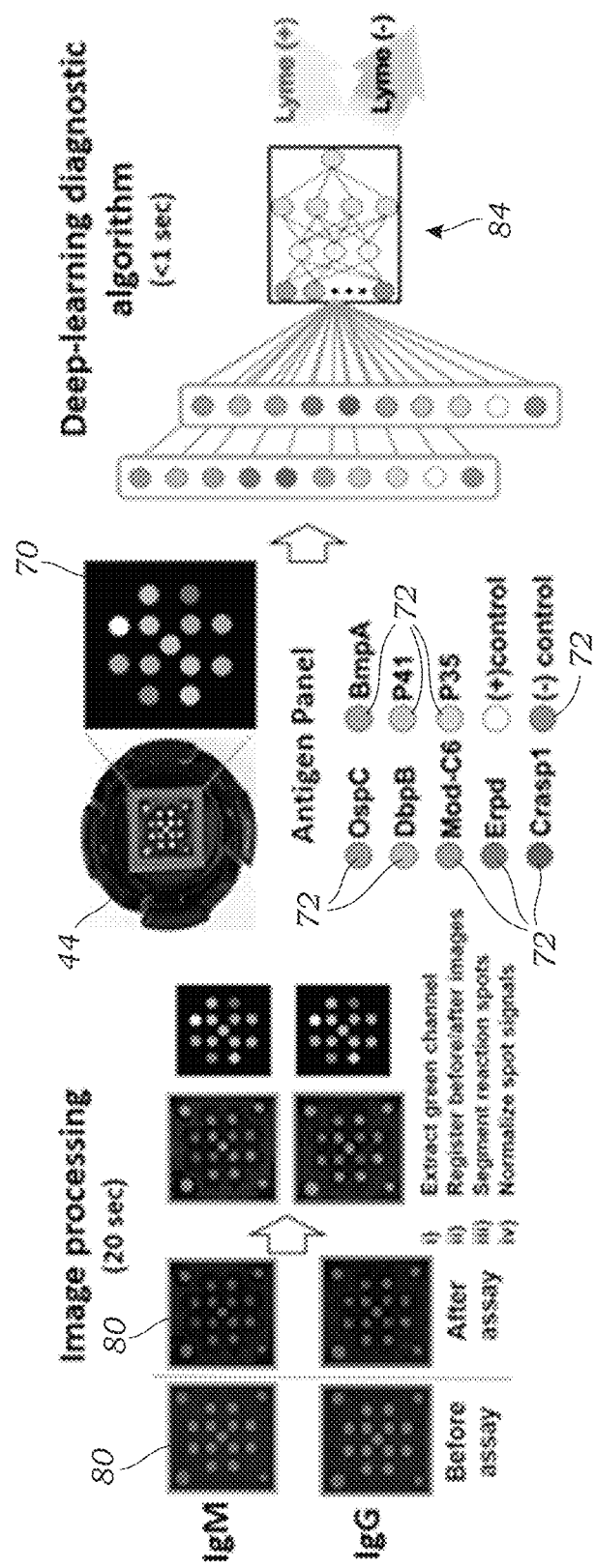
FIG. 15B illustrates image processing (left), capture antigen panel (middle), and deep learning-based analysis (right) of the multiplexed sensing membrane.
Figure 17A:
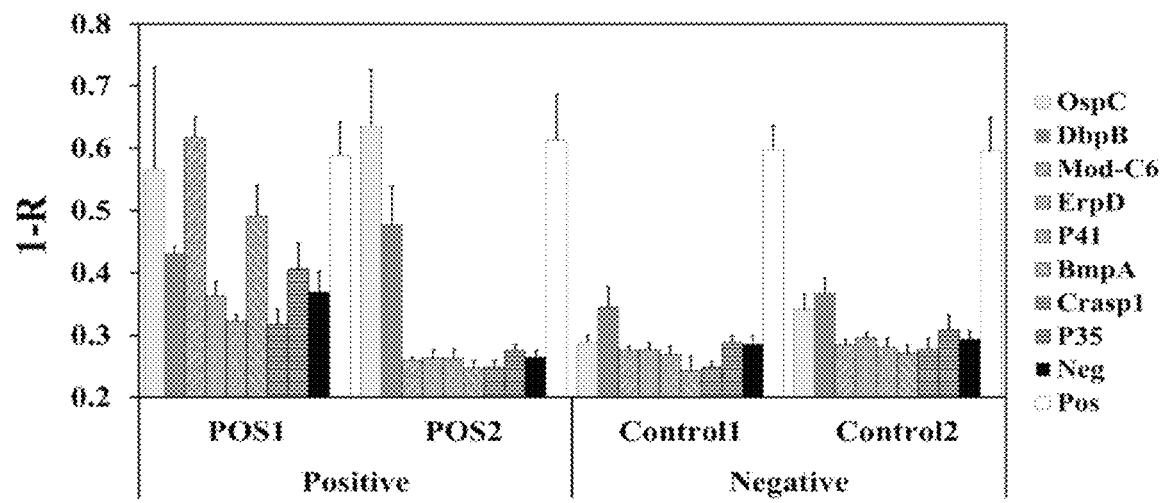
FIGS. 17A and 17B illustrates the mean (1−R) signals and standard deviations of the two seropositive (POS1 and POS2) and two seronegative (Control 1 and 2) for the IgM (FIG. 17A) and IgG sensing membrane (FIG. 17B).
Figure 17B:
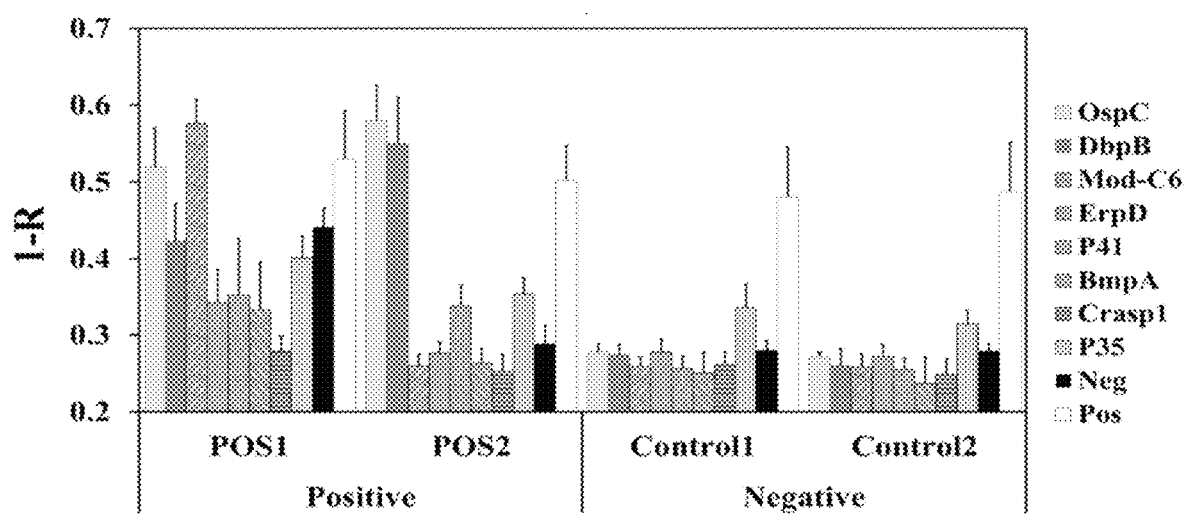

In another embodiment, the multiplexed immunodiagnostic assay system 4 operates using analysis software 84 having a trained deep neural network as illustrated in FIGS. 6 and 15A, 15B. In this embodiment, rather than use k/s statistics for each spot or location 72, normalized pixel intensities (without using k/s statistic) are calculated for each spot or location 72 and are input the analysis software 84 having a trained deep neural network. The trained deep neural network outputs or generates a diagnosis or indication of the sample that is tested. In other embodiments as explained herein, the network output may also include a concentration or concentration range of one or more biomarkers. In a specific embodiment described herein for the early detection of Lyme disease, two cassettes 40a, 40b are used with one cassette 40a including a second top or upper portion 50a that includes a conjugation layer or pad 58 that has embedded antibody-conjugated nanoparticles 66 (e.g., AuNPs) specific to LD-specific IgM antibodies captured on the sensing membrane 70. The other cassette 40b includes a second top or upper portion 50b that includes a conjugation layer or pad 58 that has embedded antibody-conjugated nanoparticles (e.g., AuNPs) specific to LD-specific IgG antibodies captured on the sensing membrane 70. The bottom or lower portion 44a, 44b of the cassettes 40a, 40b is the same for each cassette 40a, 40b.

During the assay operation when buffer, wash, or other reagents are loaded into the cassettes 40a, 40b antibody-conjugated nanoparticles 66 then bind to the LD-specific IgM or IgG antibodies previously captured on the sensing membrane 70, resulting in a color signal in response to the captured amount. After completion of these sandwich immunoreactions, both the IgM and IgG assays, which may be run in parallel, the second top/upper portions 50a, 50b and lower/bottom portions 44a, 44b of the cassettes 40a, 40b are separated from one another and the lower/bottom portions 44a, 44b containing the sensing membrane 70 are then secured to the portable reader device 10 (FIGS. 1A, 7) and immediately imaged which captures the background image 80 (taken before the assay operation) and the signal image 80 (taken after the assay operation) (FIGS. 6, 15A, 15B) of the sensing membrane 70 for subsequent analysis in a computing device 90 using image processing software 82 and analysis software 84 as described herein, where a trained neural network is used to ultimately determine the final result (seropositive or seronegative).

The trained neural network of the analysis software 84 may run on a separate computing device 90 that is local with respect to the portable reader device 10. Alternatively, the trained neural network of the analysis software 84 may run on a remote computer (e.g., remote server(s) or cloud computer(s)). In yet another embodiment, the trained neural network of the analysis software 84 may even run on the portable electronic device 14 (e.g., Smartphone) that is used to capture the images 80. The trained neural network of the analysis software 84 is designed as a diagnostic decision neural network that outputs a positive or negative indication for the particular sample being tested. The response of the network is quick outputting a result within a few seconds or even less than a second.

While the cassette 40 embodiments have largely been described in the context of a single cassette 40 including a two top portions, namely a first top portion 42 and a second top portion 50 in another alternative embodiment, only a single top portion 50 is used which includes the conjugation pad 58 therein. In this embodiment, analyte binding in the sensing membrane 70 occurs concurrently with the binding of the antibody-conjugated gold nanoparticles 66. This embodiment may be less sensitive but is more convenient to use.

In addition, while antibody-conjugated plasmonic (e.g., gold) nanoparticles 66 are described as being loaded into the conjugation pad 58 it should be appreciated that other bioconjugation tags may be loaded in the conjugation pad 58. This includes, by way of example, fluorescent molecules or dyes, enzymes, proteins or protein fragments, nucleic acids, nanometer or micrometer-sized particles, or other labeled biomolecules.

In addition, while the spots or locations 72 in the sensing membrane 70 have been described as being isolated from one another using a wax or other hydrophobic substance as a barrier, in alternative embodiments, one or more physical barriers may be used to isolate the various spots or locations 72 from one another. For example, the spots or locations 72 may be formed on a porous media such as paper and then cut or punched-out and inserted into or onto another substrate or holder that that has barriers formed therein. The barriers may be physically formed in the substrate or holder such as wells, apertures or the like that functions as a barrier. The spots or locations 72 may also be adhered or glued to another substrate that effectively creates a barrier between spots or locations 72.

Experimental

A multiplexed immunodiagnostic assay system 4 was experimentally evaluated that used a trained neural network as part of the analysis software 84 to output or generate a diagnosis or indication for Lyme disease from human serum samples. The portable reader device 10 was mobile phone-based (LG G4H810 Smartphone) (i.e., used a mobile phone as the portable electronic device 14) and used a 3-D printed (Dimension Elite, Stratasys) opto-mechanical attachment 12 containing four (4) 525 nm wavelength light emitting diodes (LEDs) 20 for even illumination of the sensing membrane 70. An external lens 28 was also mounted in the 3-D printed opto-mechanical attachment 12 below the built-in phone camera lens system for enabling an in-focus field of view. All the images 80 were obtained in raw dng format using the standard Android camera app of the Smartphone device 14.

Materials and Methods

*Borrelia burgdorferi* recombinant antigens were purchased from Prospec Inc ((OspC (BOR-004), BmpA (BOR-006), P41(BOR-001), DbpB (BOR-007) and OspA(BOR-013)), Rockland Immunochemicals Inc (Crsasp1 (000-001-C18), ErpD (000-001-009), P35 (000-001-C12)), and MyBioSource, Inc. (VlsE1 (MBS145939)). The modified-C6 and specific p41 epitope containing peptide (Mod-C6) was obtained from Biopeptides Corp. Anti-Human IgG/IgM (ab99741/ab99770) were purchased from Abcam. Anti-mouse IgG (1036-01) was purchased from SouthernBiotech. Blocker™ Bovine Serum Albumin (BSA) (37525) was purchased from Bio-Rad. Nitrocellulose membranes (0.22 μm (11327) and 0.45 μm (11036)) were purchased from Sartorius Stedim North America Inc. A vivid plasma separation membrane (grade GX) was purchased from Pall Co., and the sample pad (CF7) as well as the conjugation pad (Grade Standard 14) were sourced from GE Healthcare Biosciences Corp. The absorbent pad (Whatman Grade 707) was acquired from OpticsPlanet, Inc. The gold colloidal solution (40 nm colloid, 15707-1) was purchased from Ted Pella, Inc. Foam tape (Super-Cushioning Food-Grade Polyethylene Foam Sheets 1/16") was purchased from McMaster-Carr. A summary of the purchased materials can be found in the Tables 1 and 2 below.

TABLE 1

| No. | Layers | Product Name | Vendor | Thickness (mm) | Dimensions (cm × cm) | Cost/test (¢) |
|---|---|---|---|---|---|---|
| 1 | Absorption layer | Vivid GX ™ | Pall | 0.3 | 1.2 × 1.2 | 1.8 |
| 2 | Vertical flow diffuser (VFD) | 0.45 μm Nitrocellulose Blotting Membrane | Sartorius | 0.1 | 1.2 × 1.2 | 5.4 |
| 3 | 1st spreading layer | Vivid GX ™ | Pall | 0.3 | 1.2 × 1.2 | 1.8 |
| 4 | Conjugation pad | Standard 17 | GE Healthcare Biosciences | 0.37 | 1.15 × 1.15 | 1.6 |
| 5 | Inter pad | CF7 | GE Healthcare Biosciences | 1.87 | 1.2 × 1.2 | 3.5 |
| 6 | $2^{nd}$ spreading layer | Vivid GX ™ | Pall | 0.3 | 1.4 × 1.4 | 2.5 |
| 7 | Supporting layer | 0.45 μm Nitrocellulose Blotting Membrane | Sartorius | 0.1 | 1.7 × 1.7 | 10.7 |
| 8 | Antigen panel | 0.22 μm Nitrocellulose Blotting Membrane | Sartorius | 0.1 | 1.7 × 1.7 | 5.4 |
| 9 | Absorbent layer x5 | Grade 707 Blotting Pad | OpticsPlanet | 2.6 | 1.2 × 1.2 | 9.5 |
| 10 | Foam Tape | Food-grade foam tape | MacMaster | 1.6 | 1.7 × 1.7 | 1.3 |
| | | | | | Cost total/test | 42.2 |

TABLE 2

| Name | | Vender | Cat. No. | Quantity | Cost($) | Cost($)/Test |
|---|---|---|---|---|---|---|
| Gold nanoparticles | | Ted Pella, Inc. | 15707-1 | 100 mL | 274 | 0.21 |
| Anti-human Ab | Ant-IgG | abcam | ab99770 | 250 ug | 300 | 1.80 |
| | Anti-IgM | abcam | ab99741 | 250 ug | 300 | |
| Antigens | OspC | PROSPEC | BOR-004 | 1000 ug | 3600 | 0.58 |
| | DbpB | PROSPEC | BOR-007 | 1000 ug | 3600 | 0.58 |
| | Mod-C6 | | | | | |
| | ErpD | Rockland Immunochemicals inc. | 000-001-C09 | 100 ug | 325 | 0.28 |
| | Crasp1 | Rockland Immunochemicals inc. | 000-001-C18 | 100 ug | 325 | 0.28 |
| | BmpA | PROSPEC | BOR-006 | 20 ug | 120 | 0.14 |
| | P41 | PROSPEC | BOR-001 | 100 ug | 150 | 0.13 |
| | P35 | Rockland Immunochemicals inc. | 000-001-C12 | | 325 | 0.28 |
| 2nd antibody(anti-mouse IgG) | | SouthernBiotech | 1036-01 | 1 mg | 45 | 0.0 |
| | | | | | Sub total | 4.28 |

The Multiplexed Vertical Flow Assay (xVFA)

The multiplexed immunodiagnostic assay device 2 (which may also be referred to herein as (xVFA)) includes a stack of porous layers 54 (e.g., functional paper layers in one embodiment) and a sensing membrane 70 contained within 3-D printed plastic cassettes 40 (one for IgG and one for IgM). The cassettes 40 are divided into top/upper portions 42, 50 and bottom/lower portions 44 which can be separated through a twisting mechanism, revealing the multiplexed sensing membrane 70 on the top layer of the bottom/lower portion 44. The sensing membrane 70 contains thirteen (13) immunoreaction spots or locations 72 defined by a black wax-printed barrier, where each spot 72 is pre-loaded with a different capture-antigen or antigen epitope-containing peptide as well as proteins serving as positive- and negative-controls to enable multiplexed sensing information within a single test (FIG. 3) (in some embodiments multiple spots 72 may be duplicates, etc.). For each xVFA, there are two top/upper portions 42, 50 used during the operation (FIG. 1B). The first top/upper portion 42 facilitates the uniform flow of a serum sample from the loading inlet 52 to the sensing membrane 70, where LD-specific antibodies are bound to the detection antigens immobilized on the nitrocellulose surface. The second top/upper portion 50 is then used for color signal generation, where a conjugation pad 58, upon wetting, releases embedded gold-nanoparticles 66 (AuNPs) conjugated to anti-human IgM or IgG antibodies. The AuNPs 66 then bind to the LD-specific IgM or IgG antibodies previously captured on the sensing membrane 70, resulting in a color signal in response to the captured amount. A detailed breakdown of the functional stack of porous layers 54 and assay reagents can be found herein regarding the details of the fabrication of the multiplexed immunodiagnostic assay device 2 device (see e.g., FIG. 4A, 10, 11) along with further discussion on the wax-printed sensing membrane design and optimized operational protocol (FIGS. 10A-10D).

Preparation of Antibody—AuNPs Complexes and Conjugate Pads

Complexes of mouse anti-human IgM/IgG on AuNPs 66 were achieved by adding 100 μL 0.1M borate buffer (pH 8.4) and 20 μL of antibody (0.5 mg mL$^{-1}$) to 1 mL gold nanoparticle solution (40 nm, 1 OD) in a sterile Eppendorf tube. The mixture was incubated for one hour at room temperature, then 100 μL of 1% BSA in phosphate-buffered saline (PBS) was added as a blocking buffer. After blocking for 30 minutes at 25° C., the mixture was incubated at 4° C. for one hour. To remove excess mouse anti-human IgG/IgM, the complexes were centrifuged at 4° C. for 15 min at 8000 rpm, and washed 3 times by 1 mL washing buffer (10 mM Tris buffer (pH 7.2)). The supernatant was then re-suspended in 100 μL 0.1 M pH 8.5 borate buffer, containing 0.1% BSA and 1% sucrose. The final concentration of the antibody—AuNPs complexes was determined by optical density measurement at 525 nm using a well-plate reader (Synergy 2 Multi-Mode Microplate Reader, BioTek Instruments, Inc.). Only the complexes which had 2 OD were applied to the conjugation pad 58. 70 μL of the conjugate solution was then pipetted onto each conjugation pad 58 (1.15×1.15 cm), which had previously been blocked by 1% BSA in 0.1 M borate buffer (pH 8.5). The pads were dried at 37° C. for 30 min.

Preparation of Multiplexed Sensing Membrane and Functional Paper Layers

The multiplexed sensing membrane 70 was produced using a 0.22 μm NC membrane and wax printer (Colorqube 8580DN, Xerox). Thirteen (13) spatially isolated immunoreaction spots 72 were defined by wax-printed barriers, allowing for different capture antigens to be spotted on the nitrocellulose membrane. After printing, the sensing membranes 70 were incubated for 30 sec at 120° C. in an oven to allow the printed wax to melt and diffuse downward into the nitro-cellulose. Each of the thirteen (13) isolated sensing spots was then loaded by hand-pipetting 0.8 μL of 0.1 mg mL$^{-1}$ capture-antigen solution (1 mg mL$^{-1}$ for Mod-C6), and allowed to dry for 30 minutes at room temperature. The membrane 70 was then submerged in 1% BSA in PBS solution for 30 min to block non-specific binding, and again dried for 10 min at 37° C. in a convection dry oven. The supporting layer 64 (0.22 μm pore-size NC membrane) and vertical flow diffuser layer 60 (0.45 μm pore-size) were also patterned with a wax printer, and the BSA blocking procedure was performed for these paper layers following the same procedure as for the multiplexed sensing membrane 70. The absorbent pad 56 (1.2×1.2 cm), foam tape (1.7×1.7 cm for outside, 1.2×1.2 cm for inside dimensions), and asymmetric membrane (1.2×1.2 cm for absorption layer and 1$^{st}$ spreading layer 62 and 1.4×1.4 cm for 2$^{nd}$ spreading layer 62) were all laser-cut (60 W Speedy 100 CO$_2$ laser from Trotec) to achieve precise dimensions.

Assembly of the Multiplexed Vertical Flow Assay (xVFA)

A 3-D printed cassette 40, which opens, closes, and locks through a simple twisting mechanism using posts, detents, or bosses 46 that interface with a slot or recess 48 (FIG. 1E) was custom-developed for housing the vertical stack of paper layers 54. Prepared paper materials were stacked inside of the cassette 40 as follows; for the top/upper portions 42, 50; asymmetric membrane (absorption layer 56), vertical flow diffuser layer 60, 1$^{st}$ spreading layer 62, conjugation pad 58 (only for 2$^{nd}$ top/upper portion 50), sample pad 56, asymmetric membrane (2$^{nd}$ spreading layer 62) and supporting layer 64, for the bottom/lower cassette portion 44; multiplexed sensing membrane 70 and five absorbent pads 56 (FIG. 4A). In case of top absorption layer 56, the face with the smaller pore-size was contacted with lower layer, with the stacking reversed for the 1$^{st}$ and 2$^{nd}$ spreading layers 62. The outer edges of the supporting layer 64 in the top/upper portions 42, 50 and the multiplexed sensing membrane 70 in the bottom cassette portion 44 were secured with foam tape to protect the sensing membrane 70 from potential shifting or damage. Glue or other adhesive may also be used.

Characterization of the Vertical Fluid Flow in xVFA Design

The vertical flow properties of the xVFA were evaluated to better understand the underlying performance of the test as well as to optimize the operational protocol. Specifically, the signal strength versus the flow rate was investigated and the incubation time with a design constraint of 15 min assay time in order to be on-par with standard POC tests and lateral flow assays (LFAs).

Flow Rate and Signal Intensity Versus Wax-Coverage of Sensing Membrane

The vertical flow rate in the xVFA cassette 40 is limited by the flow-through area (void area) of the multiplexed sensing membrane 70 (i.e., the space absent from the wax-printed barrier) and as a result has a clear effect on the colorimetric signal intensity. To empirically understand this relationship, sensing membranes 70 with four open reaction spots, yet different proportions of wax coverage (60%, 80%, 90%, and 95% of the 2-D membrane area) were tested in the xVFA (see FIGS. 10A, 10B). By loading increments of fixed-volumes of the running buffer into the first top/upper cassette portion 42 and recording the time it took for the fluid to absorb completely, the flow rate of the sensors was calculated for xVFA containing membranes 70 with different wax coverage. The signal strength was then evaluated by the (1−R) signals (see Eq. 3) produced by immunoreaction spots functionalized with the positive control proteins (Rabbit anti-Mouse IgG). The ratio of the control protein solution volume to each spot's area, 0.7 μL mm$^{-2}$, was conserved for the different sensing membranes 70.

Figure 10A:
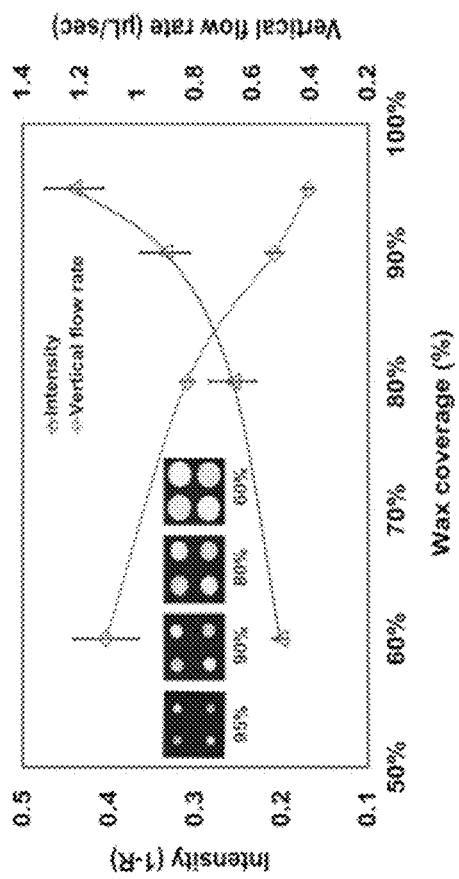
FIG. 10A illustrates the vertical flow rate at the loading inlet versus time shown for sensing membranes with different percentage of wax coverage.
Figure 10B:
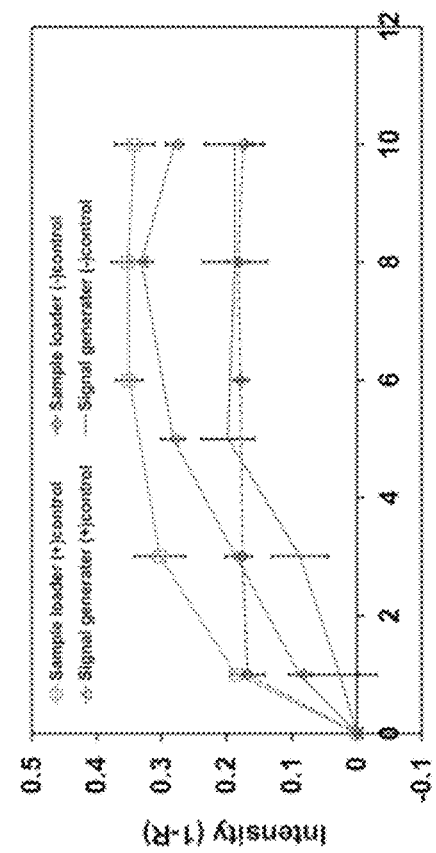
FIG. 10B illustrates the colorimetric signal intensity and vertical flow rate versus different percentage of wax coverage.

At the beginning of the sample injection, the flow rate is at its fastest before it slows, converging to near constant flow rate that is limited by the flow-through area of the wax-printed sensing membrane 70. As shown in FIG. 10B, the 95% wax printed membrane 70 shows the highest signal intensity with the steadiest flow rate over time. However, due the slower overall flow rate this sensing membrane 70 design requires around 10 min to fully absorb the running buffer, sample, and washing buffer. In contrast, 60%, and 80% wax-coverage on the sensing membrane 70 can complete absorption within 3 min, but with less uniformity in the sample flow over time. Therefore, due to this time-uniformity trade-off, the sensing membranes 70 with 90% wax-coverage were utilized.

Flow Rate and Signal Intensity Versus Loading Time

Figure 10C:
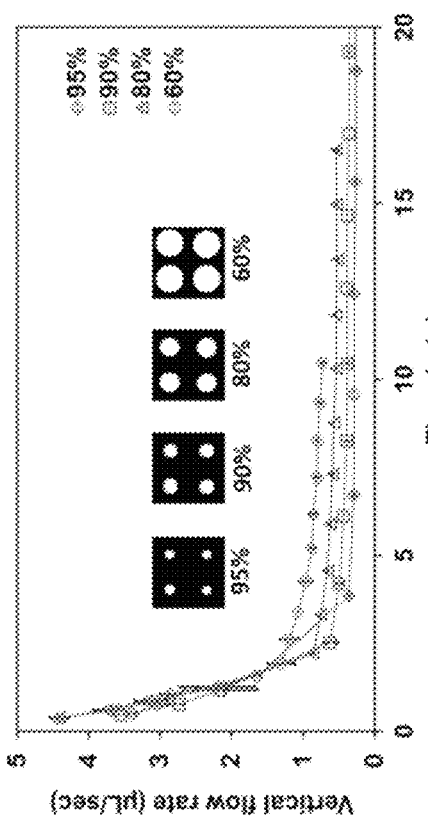
FIG. 10C illustrates the vertical flow rate at the loading inlet verses time for the $1^{st}$ top/upper cassette (sample loader) and $2^{nd}$ top/upper cassette (signal generator) with a sensing membrane containing 90% wax coverage.
Figure 10D:
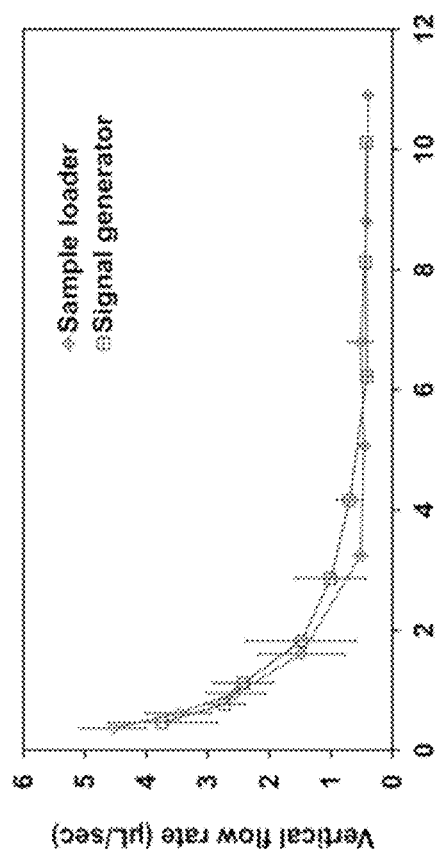
FIG. 10D illustrates the colorimetric signal intensity versus time of the positive and negative control immunoreaction spots.

The flow rate and signal intensity (1−R) for the first top/upper cassette portion 42 (sample loader) was recorded over time as described herein (FIGS. 10C, 10D). The flow rate and signal intensity for the second top/upper cassette portion 50 (signal generator) was also determined, however prior to analysis, the xVFA was assembled with the first top/upper cassette portion 42 and run according the standard protocol outlined herein. The xVFA cassette 40 was then opened and the sampler top/upper cassette portion 42 was exchanged with the signal generator top/upper cassette portion 50. The flow rate over time was recorded following the same procedure for the first top/upper cassette portion 42, with a sensing membrane 70 containing 90% wax-coverage (FIGS. 10C-10D).

As shown in FIG. 10D, the sample loader top/upper cassette portion 42 reached a steady flow rate and signal intensity after approximately 6 min, while it took nearly 8 min for the signal generator top/upper cassette portion 50. Based on these observations, a 6 min and 8 min incubation time was chosen for the first and second top/upper cassette portions 42, 50 respectively to help support the flow and signal repeatability as well as rapid assay time (15 min).

xVFA Fabrication Issues that were Observed

In the second sample-pull testing, four IgM sensing membranes 70 exhibited failed positive control spots, due to the accidental incorporation of non-functionalized (blank) sensing membranes 70 during the xVFA assembly. This fabrication error was identified through qualitative observations at the time of testing, and was also self-evident in an analysis of the positive control spots distributions (see FIGS. 11A-11F). As a result, these four xVFA tests were discarded from the testing analysis.

Additionally, in the second sample-pull testing set, three IgM and three IgG sensing membranes 70 had a scaling mismatch between the background image 80 (taken before the assay) and signal image 80 (taken after the assay) possibly due to an expansion of the sensing membrane 70 during the assay operation. This scale mismatch in the registration can lead to misaligned immunoreaction spot 72 sampling, as the background and signal images 80 are sampled with the same mask. Therefore, all sensing membranes 70 which exhibited a scaling-factor greater than 2% as defined by an affine-mapping (six in total) were automatically re-processed with an affine-transformation for correct registration and spot analysis (see FIGS. 12A-12F).

Multi-Antigen Panel Pre-Selection

Prior to the clinical study, fifteen (15) clinical samples (8 cases and 7 endemic controls, also obtained from the Lyme Disease Biobank) were tested in duplicate to screen the following nine (9) antigens and on synthetic peptide (Mod-C6) for both IgM and IgG antibody detection: OspC, BmpA, P41, ErpD, Crasp1, OspA, DbpB, VlsE, P35 and Mod-C6. The 25-spot multiplexed-sensing membrane 70 was employed for antigen screening with the antigens immobilized into the reaction spot 72 following the same methods in the clinical study (see FIG. 13A). Samples loaded into the xVFA undergo complex immunoreactions that depend greatly on the conditions in the nitrocellulose matrix where the capture antigens are immobilized. Such an environment is significantly different from conventional Enzyme-linked Immunosorbent Assays (ELISA) and Western blotting (WB) therefore, each antigen was assessed within the paper-based sensor before being implemented in the detection panel used for the clinical evaluation.

FIGS. 13A-13D shows the results of antigen pre-screening. The t-score of each detection antigen was ranked, where the t-score was defined by Welch's t-test, $$t_m = \frac{X_{m(+)} - X_{m(-)}}{\sqrt{\frac{s^2_{m(+)}}{N_{(+)}} + \frac{s^2_{m(-)}}{N_{(-)}}}} \quad \text{Eq. 2}$$

where $X_m$ and $s_m^2$ represent the mean and variance of the $(1-R_m)$ signal respectively for the seropositive and negative samples as denoted by the (+) and (−) subscripts. N represents the number of seropositive or negative samples. The capture antigens were therefore classified into three regimes: I, II, III (FIG. 13B). Regime III shows the worst discriminators, VlsE and OspA, exhibiting a t-score<1. Despite OspA and VlsE being known to be effective detection antigens for LD, no signals were derived from their immunoreactions within the xVFA system. This could be due to poor antigen immobilization due to weak charge interaction as well as interference caused by the nitrocellulose matrix, as well as due to an absence of antibodies for VlsE and OspA in the samples tested. Therefore, these antigens that fell into Regime III were not included in the panel used for the clinical study. The antigen targets in Regime II were each kept as a single immunoreaction spots 72 on the final 13 spot multiplexed-sensing membrane, while the antigen targets in Regime I, which exhibited the best discriminatory ability (t-score>2.0), were therefore each given an additional (redundant) immunoreaction spot 72, in the place of the eliminated antigens from Regime III.

Figure 14A:
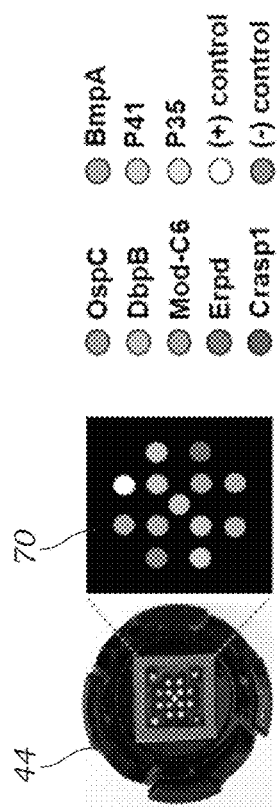
FIG. 14A illustrates the sensing membrane of the xVFA and the map of the multi-antigen panel according to one embodiment.
Figure 14B:
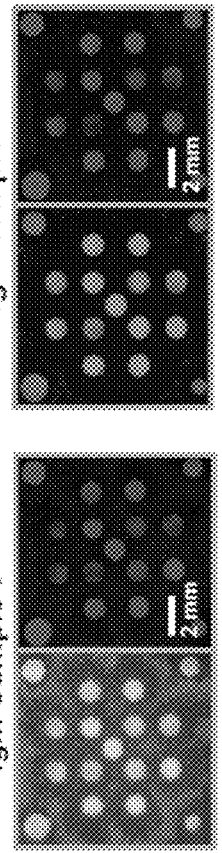
FIG. 14B illustrates example images of IgM (left) and IgG (right) sensing membranes after activated by a human serum sample (sample #7) under ambient lighting conditions and using the mobile-phone reader (under green LED illumination).
Figure 14C:
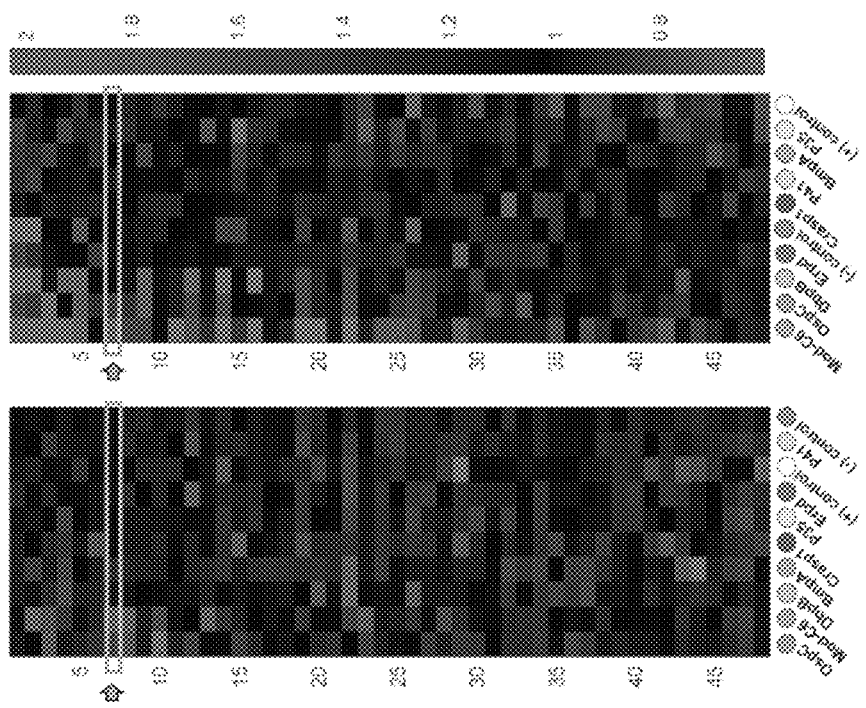
FIG. 14C illustrates the t-score (Eq. 2) of the multi-antigen channel calculated over the training data-set for the IgM (left) and IgG (right) sensing membranes ranked in descending order.
Figure 14D:
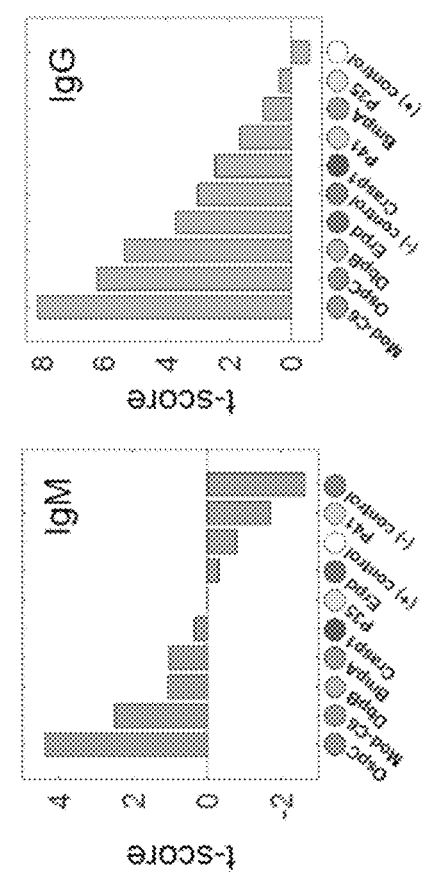
FIG. 14D is a heat map showing the signals from the multi-antigen panel of the IgM (left) and IgG (right) sensing membranes activated by the seropositive samples in the training set. The color bar represents the (1−R) signal of each sensing channel normalized to the mean signal of the same sensing channel across all the seronegative samples in the training data-set. The normalized IgM and IgG signals for sample #7 are outlined by boxes.

This strategy resulted in the final multi-antigen panel for the clinical study: two-spots 72 in the panel for Regime I (OspC, DbpB and Mod-C6), and single spots 72 for Regime II (Crasp1, Erpd, P41, BmpA and P35) along with single spots 72 for the positive and negative control proteins which were anti-mouse IgM/IgG and BSA respectively (FIG. 14A). It is important to note that the ten (10) antigens employed in this study, though commonly used for LD serology testing, are a subset of the much larger number of target antigens which have been evaluated and developed for LD diagnosis. Future iterations of the multi-antigen detection panel within the xVFA can therefore incorporate novel antigen targets produced through, for example, epitope mapping or other large-scale screening efforts.

Assay Operation

First, a background image 80 of the blank sensing membrane 70 is taken with the portable reader device 10. Then the first top/upper cassette portion 42 is mated with the bottom/lower cassette portion 44, and 200 µL of running buffer is introduced to fully wet the paper layers in the xVFA. After the buffer is absorbed fully into the xVFA cassette 40 (~20 seconds), 20 µL of serum sample is pipetted into the loading inlet 52 and allowed to absorb. Then, a second addition of running buffer is introduced to the loading inlet 52, followed by a 6-minute wait period, during which the serum sample reacts with the sensing membrane 70 and the unreacted sample is washed away to the lower absorbent pads. The first top/upper cassette portion 42 is then exchanged with the second top/upper cassette portion 50, and 450 µL of running buffer is added to release the AuNP conjugates 66 responsible for color signal generation. After an 8-minute wait period, the xVFA cassette 40 is opened and the bottom/lower cassette portion 44 is imaged by the mobile phone-based portable reader device 10 to get the multiplexed signal. Separate xVFAs cassettes 40a, 40b are run in parallel for IgM and IgG antibody detection, where the only difference between the two xVFA cassettes 40a, 40b is in the conjugation pad 58, i.e., one conjugation pad 58 contains AuNPs conjugated to anti-IgM antibodies and the other contains AuNPs conjugated to anti-IgG antibodies (FIG. 15A). The two cassettes 40a, 40b are imaged sequentially but it should be appreciated that both cassettes 40a, 40b could potentially be imaged simultaneously given a large enough field-of-view with both cassette bottom/lower portions 44 being secured to the portable reader device 10 at the same time.

Image Processing and Deep Learning-Based Analysis

Raw dng images 80 (FIG. 15B), captured by the portable reader device 10, of the sensing membrane 70 taken before (background image 80) and after (signal image 80) the assay are converted to tiff format. The green pixels are then extracted (other color), and the background and signal images are registered to each other via a rigid-transformation. The immunoreaction spots 72 are then identified in the background image and a fixed-radius mask is defined per-spot at approximately 80% of the immunoreaction spot area. The pixel intensity within this immunoreaction spot mask is then calculated for the registered signal image and normalized by the pixel average of the corresponding immunoreaction spot in the registered background image, $$R_m = \frac{\Sigma_{x,y \in \Omega_m} I_{signal}(x, y)}{\Sigma_{x,y \in \Omega_m} I_{background}(x, y)} \quad \text{Eq. 3}$$

where $R_m$ defines the normalized signal or pixel intensity per immunoreaction spot (m) and $\Omega_m$ defines the x-y bounds of the fixed-radius mask per immunoreaction spot 72. This background normalization procedure helps account for non-uniformities in the illumination as well as local defects that might exist within the immunoreaction spots 72 on each xVFA sensing membrane 70. Immunoreaction spots 72 functionalized by the same capture antigen are averaged together, and each of the unique $R_m$ signals, derived from both the IgM and IgG xVFAs, are then used for deep learning analysis (FIGS. 6 and 15B) (image pre-processing generates $R_m$ values which are input to the trained neural network of the analysis software 84).

Lastly, before being input into the diagnostic decision neural network, the $R_m$ signals from both the IgM and IgG xVFAs are standardized to the mean, $\overline{R_m}$, and standard deviation, $\sigma_m$ taken over the training set, $$R'_m = \frac{R_m - \overline{R_m}}{\sigma_m} \quad \text{Eq. 4}$$

The decision neural network (FIG. 15B, right side) contains an input layer with M nodes (e.g., M=20 with the full IgM/IgG antigen panel), three fully connected hidden layers with 128, 64, and 32 nodes, in the first, second, and third layers, respectively. The $R_m$ signals from the plurality of immunoreaction spots are input to the decision neural network. Each layer contains batch normalization, a 50% dropout, and a Rectified Linear Unit (ReLU) activation function, defined by f(x)=max (0, x), with the exception of the final output layer, which uses a sigmoid activation function, yielding a network output as a numerical value between 0 and 1. A final binary diagnosis is then made by evaluating this numerical output with a blind cutoff value of 0.5. A binary cross-entropy cost function, defined as:

$$H(y, y') = -\frac{1}{N} \sum_{n=1}^{N} [y_n \log y'_n + (1 - y_n) \log(1 - y'_n)] \quad \text{Eq. 5}$$

was used during the training phase (learning rate=0.001, batch-size=32) with the two-tier based seropositive and seronegative diagnosis used as the gold-standard label, $y_n \in \{0,1\}$. Here, N represents the number of training samples, and $y'_n \in (0,1)$ represents the neural network prediction. The hyper-parameters mentioned above (except the diagnostic threshold) were determined by a random parameter optimization in which 2 and 3 hidden layers with varying number of nodes were tested via k-fold cross-validation (k=5) along with different dropout, learning rate, and batch size parameters randomly selected from a pre-defined list. All networks were trained for up to 1000 epochs with early stopping criterion defined by the stagnation of training accuracy not exceeding a change of 0.1% over 100 training epochs. The network weights at the last epoch (defined by the early stopping criterion) were then stored in the final model.

Precision Testing

A precision evaluation was performed using the same assay operation and analysis described above. Two additional seropositive samples and two endemic control samples, were blindly tested with six repeat measurements by the same operator. To test the interoperability of the xVFA, two volunteers who had no experience with the xVFA operation were trained for five (5) minutes before each performing duplicate measurements with one seropositive sample and one endemic control.

The importance of the batch-specific standardization is especially highlighted by this precision testing which similarly shows a drift in the network output without batch-specific standardization. However, by performing the input standardization with the mean and standard deviation of the batch used for precision testing, the overall accuracy during the precision testing results falls in line with the blind-testing performance, and showed no apparent instability between the operators (FIG. 16). The individual immunoreactions were also examined in terms of their precision (FIGS. 17A-17D).

Clinical Study

In total, 106 unique human serum samples were obtained from the LDB (collected under Advarra IRB Pro00012408). Out of these sample, 50 were used for training, 50 for blind testing, with the additional 6 used for precision evaluation. All the samples used were early-stage LD, having been obtained <30 days since symptoms or the initial tick bite. All the cases and endemic controls were confirmed to be Lyme-positive or negative through standard two-tier testing methods, or in some cases quantitative Polymerase Chain Reaction (qPCR) or convalescent draws (seroconversion). For the first tier, a combination of Whole Cell Lysate Enzyme-linked Immunosorbent Assay (ELISA), C6 Peptide EIA, or VlsE/PepC10 ELISA testing was used. The second tier, performed regardless of the first-tier results, was comprised of the standard IgM and IgG WB. Samples were considered seropositive if any of the three EIA tests in the first tier had a positive or equivocal (borderline) result and the second tier had a positive result for either the IgM or IgG WB as defined by the CDC recommendation ($\geq 2$ of 3 bands for IgM WB, and $\geq 5$ of 10 bands for IgG). Samples were also considered seropositive by MTTT guidelines, where a seropositive diagnosis was called from two positive or equivocal EIA tests along with the presence of EM, without the need for a positive WB result. Additionally, all samples were confirmed negative for coinfections of Anaplasmosis and *Babesia*, both of which are infections also transmitted by the *Ixodes* tick and can produce similar constitutional symptoms to LD.

The clinical samples used for training and testing were obtained and tested in two separate sample-pulls. The first sample-pull contained 25 LD cases and 25 endemic controls from a collection site in East Hampton, New York between 2014 and 2016. Twenty-four (24) of the twenty-five (25) LD cases were seropositive, with the one exception confirmed Lyme-positive through *B. burgdorferi* qPCR. All seropositive samples were early-stage LD, with 3 out of 24 being early disseminated, defined by the presence of multiple EMs. All samples in the first sample-pull were tested with the IgM and IgG xVFAs in duplicate and used as the training data-set ($N_{(+)}=48$, $N_{(-)}=52$). It should be emphasized that since the training ground truth is the two-tier test (which may be replaced using the paper-based POC xVFA), one of the Lyme-positive samples here (tested in duplicate) has been added to the negative set ($N_{(-)}=52$) since it was seronegative (although being qPCR positive).

The second sample-pull, used for blind testing of the system 4, also contained twenty-five (25) LD cases and twenty-five (25) endemic controls, but was obtained fully blinded (i.e., without case and control labels), and tested with the xVFAs and the associated serodiagnostic algorithm three months after the first sample-pull. The second sample-pull also contained cases and endemic controls from collection sites in East Hampton (USA), New York (USA), but also included samples from several sites in Wisconsin (USA), which were not included in the training phase. In this blind testing set, twenty-three (23) of the twenty-five (25) LD cases were seropositive, with the two exceptions confirmed Lyme-positive through a convalescent blood-draw taken approximately three (3) months after the first draw that revealed seroconversion via two-tier testing methods. All seropositive samples were early-stage LD, with nine (9) out of twenty-three (23) being early disseminated. All the samples in the second sample-pull were tested with the IgM and IgG xVFAs in duplicate and used as a blinded test set ($N_{(+)}=42$, $N_{(-)}=54$), with four IgM tests removed due to fabrication error (see FIGS. 11A-11F). The seropositive and negative diagnostic predictions resulting from the xVFA testing and machine learning algorithm were blindly sent to the LDB prior to receiving the gold-standard testing labels (to determine blind testing performance). Six sensing membranes 70 were additionally processed (compared to other activated xVFAs) using an affine image transformation to correct misalignments resulting from unforeseen expansion and/or contraction of the nitrocellulose pad, during the automated image registration step (see FIGS. 12A-12E).

Lastly six separate serum samples, obtained at the same time as the second sample pull were used for precision evaluation performed by a single assay operator as well as multiple, newly trained personnel. In summary, 106 unique human serum samples obtained from the LDB have been used for training, testing and further inspection of the multiplexed immunodiagnostic assay device 2 and system 4.

Results

Training and cross-validation. The first sample-pull ($N_{(+)}=48$, $N_{(-)}=52$) was used entirely for cross-validation and training of the xVFA platform. FIGS. 14A-14D summarizes the signals from the multi-antigen detection panel across all the seropositive samples in the training set, with the raw (1−R). The statistical performance of each antigen in terms of its t-score (Eq. 2) is also shown (FIG. 14C), with the Mod-C6 peptide and OspC antigen being the top-ranked immunoreaction spots for the IgG and IgM sensing membranes respectively. As discussed herein, the individual performance and therefore the value of different antigen-targets as a single disease discriminator is highly-limited in the context of LD diagnosis, and the multiplexed xVFA platform computationally selects a complementary set of antigen-targets that collectively diagnose early-stage LD, providing a cost-effective and rapid POC replacement for the two-tier test.

Before training the final serodiagnostic algorithm to be used for the detection of early-stage LD, the training set was used for selecting an optimal subset of antigens. A sequential forward feature selection (SFFS) method was implemented where the signals from each sensing channel were added one at a time, into the input layer of the neural network and then trained via k-fold (k=5) cross-validation. After the addition of each input feature, the performance of the network was evaluated based off a mean square error cost function, i.e., $$J(y, y') = \frac{1}{N} \sum_{k=1}^{5} \sum_{i=1}^{\frac{N}{5}} (y_{i,k} - y'_{i,k})^2 \qquad \text{Eq. 6}$$

where $y_{i,k} \in \{0,1\}$ is the ground truth binary result (i.e., seropositive or negative) and $y_{i,k}' \in (0,1)$ is the numerical output of the network for the $i^{th}$ test in the $k^{th}$ fold of the k-fold cross validation (k=5). N is the number of tests in the training data-set. The input feature which yielded the best network performance for that iteration was then kept as an input feature until all the twenty (20) sensing channels were included as inputs (for ranking of their collective value for LD diagnosis); see e.g., FIG. 18C.

FIG. 18A shows the area under the receiver operator characteristic (ROC) curve (i.e., AUC) at each round of the SFFS antigen-selection algorithm, revealing a local maximum (AUC=0.969) created by a panel of six (6) antigens and the three (3) control spots: OspC, P41, and the positive control spot (anti-mouse IgM) from the IgM sensing membrane, as well as the Mod-C6 peptide, Crasp1, BmpA, P41, positive control spot (anti-mouse IgG), and the negative control spot (Bovine Serum Albumin, BSA) from the IgG sensing membrane. Using this subset of sensing channels as the detection panel, a sensitivity of 91.7% and specificity of 96.2% was found via the cross-validation analysis (FIG. 18A, inset). The final LD diagnosis network was then trained using this computationally-selected subset as the antigen panel (M=9), incorporating the tests (i.e., 100 activated xVFAs) from the first sample-pull ($N_{Train}$=100, i.e., $N_{(+)}$=48 and $N_{(-)}$=52), using the same network parameters outlined above.

Figure 19:
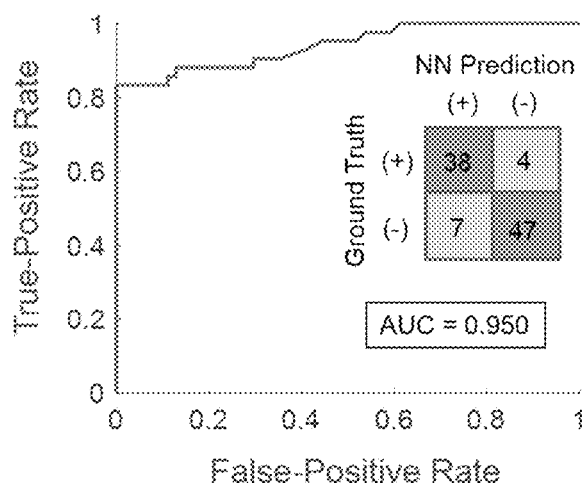
FIG. 19 illustrates the ROC curve for the blind testing data (NTest=96) as output from the neural network trained with the nine (9) selected antigens (see FIG. 18C) from the training set ($N_{Train}$=100). The inset shows the confusion matrix and area under the ROC curve (AUC). The table to the right summarizes the performance over the blindly-tested LD human serum samples with respect to the two-tier testing method.
Figure 20A:
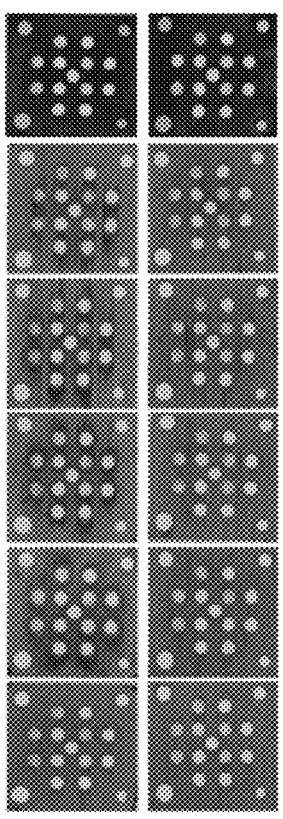
FIGS. 20A-20D illustrate images (under ambient light conditions) of the IgM and IgG sensing membranes activated by two seropositive samples and two endemic controls, with six repeat measurements for each sample performed by the same operator.
Figure 20B:
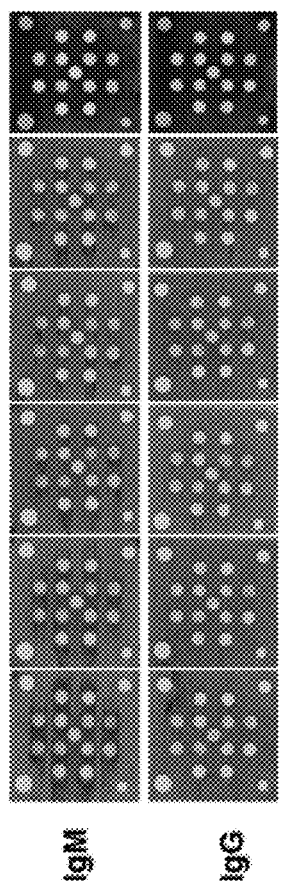
Figure 20C:
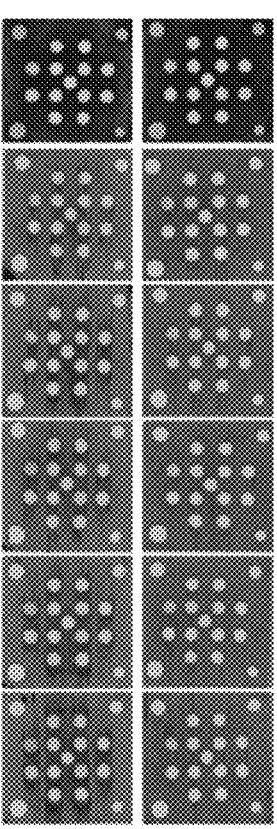
Figure 20D:
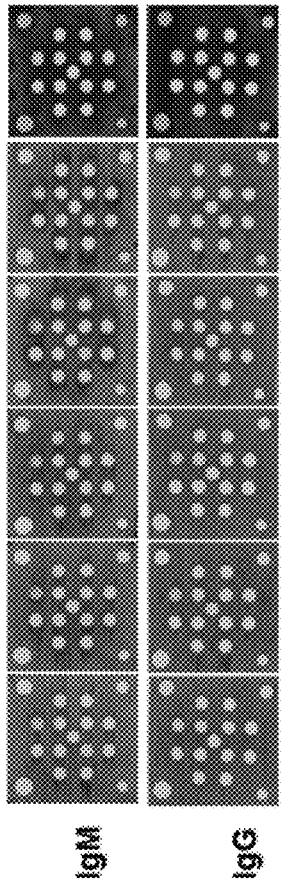

Clinical blind testing. The second sample-pull ($N_{(+)}$=42, $N_{(-)}$=54) was then entirely used for blind testing the performance of the xVFA diagnostic platform, yielding an AUC of 0.950, sensitivity of 90.5%, and specificity of 87.0% with respect to the seropositive and seronegative results, as summarized in FIG. 19. This reported diagnostic performance of the xVFA device 2 and system 4 achieved during the blind testing phase is believed to exceed previous POC tests for early-stage LD. As a point of reference, Tables 3 and 4 below show a comparison with the recently FDA-approved POC test from Quidel, which can be used as a first-tier test, detecting IgM and IgG antibodies using the C6 antigen.

TABLE 3

| | | xVFA (threshold = 0.5, Blind testing) | | | xVFA (threshold = 0.66, Batch standardization) | | | Standard Two-Tier Serology | | |
|---|---|---|---|---|---|---|---|---|---|---|---|
| | N* | Pos | Neg | % Agreement with clinical status | Pos | Neg | % Agreement with clinical status | N | Pos | Neg | % Agreement with clinical status |
| Endemic Controls | 50 | 7 | 43 | 86.0% | 2 | 48 | 96.0% | 25 | 0 | 25 | 100% |
| Early Lyme Positive | 46 | 38 | 8 | 82.6% | 36 | 10 | 78.3% | 25 | 21 | 4 | 84.0% |

TABLE 4

| | | Sofia Lyme IgM | | | Sofia Lyme IgG | | |
|---|---|---|---|---|---|---|---|
| | N | Pos | Neg | % Agreement with clinical status | Pos | Neg | % Agreement with clinical status |
| Endemic Controls | 190 | 33 | 157 | 82.6% | 25 | 165 | 86.8% |
| Early Lyme Positive | 60 | 49 | 11 | 81.7% | 49 | 11 | 81.7% |

Though FDA-approved, the Quidel test is not recommended as a replacement of the two-tier testing. The performance of the xVFA device 2 and system 4 also outperforms a number of previous clinical studies investigating diagnostic performance of standard two-tier as well as modified two-tier testing with respect to the ultimate clinical diagnosis.

Next, to achieve higher specificity, the decision threshold of the diagnostic network was tuned during the training phase such that the cross-validation specificity reached >98%, resulting in a decision threshold of 0.66. Implementing this threshold in the blind testing phase (with 192 activated xVFAs), along with batch-specific standardization, an AUC, sensitivity and specificity of 0.963, 85.7% and 96.3%, respectively, were achieved with respect to the two-tier serology results as seen in Table 5 below.

TABLE 5

| | | | xVFA (threshold = 0.5, Blind testing) | | | xVFA (threshold = 0.66, Batch standardization) | | |
|---|---|---|---|---|---|---|---|---|
| | | N | Pos | Neg | % Agreement with clinical status | Pos | Neg | % Agreement with clinical status |
| Two Tier testing | Seronegative controls | 54 | 7 | 47 | 87.0% | 2 | 52 | 96.3% |

TABLE 5-continued

| | | N | xVFA (threshold = 0.5, Blind testing) | | | xVFA (threshold = 0.66, Batch standardization) | | |
|---|---|---|---|---|---|---|---|---|
| | | | Pos | Neg | % Agreement with clinical status | Pos | Neg | % Agreement with clinical status |
| | Early Lyme Seropositive | 42 | 38 | 4 | 90.5% | 36 | 6 | 85.7% |
| Two-tier testing + PCR + Seroconversion | Negative controls | 50 | 7 | 43 | 86.0% | 2 | 48 | 96.0% |
| | Early Lyme Positive | 46 | 38 | 8 | 82.6% | 36 | 10 | 78.3% |

Such optimization of the decision biases can be utilized to achieve a desired false-positive and false-negative trade-off, depending on the clinical setting where the LD test is administered.

With this fine-tuned decision threshold, two false positive and six false negative results were achieved out of the ninety-six (96) individual tests run through the xVFA system 4, reaching an overall accuracy of 91.7%. Interestingly, some intuitive reasoning can be attributed to these instances of misdiagnosed tests. For example, in four out of the six, the instances of false negative tests were from two patients that self-reported the shortest duration of LD symptoms (≤1 day) indicating that these samples may have the least developed immune response in the blind testing set. Additionally, one of these two false-negative duplicate pairs was clinically positive in the first-tier due only to an equivocal result in the VlsE/PepC10 EIA. Because VlsE was eliminated from the multi-antigen detection panel during the pre-screening process, the xVFA device 2 is incapable of detecting antibodies to VlsE. This can be addressed in the future by further optimizing the binding properties of VlsE antigen in the nitrocellulose substrate 70 as well as expanding the number of diverse sera in the training set prior to the computational antigen selection.

It is also important to note that two seropositive samples in the testing set were considered negative through standard two-tier testing (STTT), i.e., where the second-tier is IgG/IgM WB. Nevertheless, the xVFA device 2 correctly called these samples positive with respect to the MTTT gold-standard label, which has demonstrated greater efficacy compared to the STTT in recent reports and has in fact lead the CDC to amend their recommendation for LD testing.

Lastly, half of the misclassified samples (4 out of 8) are from single discordant tests among the duplicate pairs. Therefore, to shed more light on this result, precision testing was performed with an additional six samples ($N_{(+)}$=3, $N_{(-)}$=3) obtained from the LDB, where each sample was measured with six repeated xVFA tests following the same operational protocol as in the training and testing phases (see FIGS. 20A-20D, 17A-17D, FIG. 16). To more realistically assess how the xVFA device 2 performs as a POC test, the precision between three different users/operators was examined, two of which were new to xVFA operation and given only 5 minutes of training. With the batch-specific standardization and threshold tuning, the overall accuracy during this precision testing, 91.7%, exactly matched the accuracy obtained during the blind testing. Additionally, no difference in accuracy was observed between the precision testing from a single operator and the testing completed by the multiple newly trained operators (FIG. 16). The precision of the individual immunoreactions was also investigated, yielding an average coefficient of variation of 8.9% for the same operator and 9.3% for the various newly trained operators (FIGS. 20A-20D, 17A-17D). While this shows good overall repeatability in the underlying immunochemistry, some antigen spots 72 exhibited a coefficient of variation exceeding 20% which can ultimately lead to poor precision in the output of the decision algorithm. Therefore, despite the demonstration of interoperability, these testing results suggest that precision might be a limiting factor of device 2 performance. Further improvements can be made by automating the fabrication processes and implementing humidity and temperature-controlled environments, in order to improve the coefficient of variation of the individual immunoreactions as part of the xVFA device 2. Additionally, ensuring that a large number of samples are used during the batch-specific standardization could potentially further improve testing precision.

Discussion

Optimization of Antigen Selection in Early-Stage LD xVFA Platform

Computationally selecting the detection panel from a larger set of antigen/peptide targets improves the performance of the serodiagnostic algorithm. The capture antigens functionalized to the sensing membrane 70 produce varying degrees of statistical variance in their optical signals, especially over different batches of fabricated sensors. This can stem from fabrication tolerances borne out of the low-cost materials, or from operational variance. Some capture antigens can also exhibit varying degrees of cross-reactivity with other antibodies native to human sera. The feature selection procedure used herein helps eliminate the least reliable discriminators while conserving an ensemble of reactions that can most reliably detect the immune response. A very good example of this phenomenon can be seen in this comparison: when forgoing the feature selection process and implementing the full antigen selection panel (M=20) as inputs to the network, the cross-validation testing reveals that AUC, sensitivity and specificity are 0.894, 72.9% and 92.3% respectively, compared to 0.969, 91.7% and 96.2% respectively, from the network trained on the computationally-selected subset of 9 features (see Table 6 below and FIGS. 18A-18D); this clearly emphasizes that the use of more antigen-targets does not necessarily offer a better solution for LD diagnosis.

TABLE 6

| | Selected Antigen Panel (M = 9) | Full Antigens (M = 20) | C6 IgG Only (M = 1) |
|---|---|---|---|
| Training Phase (N_ = 52, N_+ = 48) | | | |
| Sensitivity (FN) | 91.7% (4) | 72.9% (13) | 77.1% (11) |
| Specificity (FP) | 96.2% (2) | 92.3% (4) | 98.1% (1) |
| AUC | 0.969 | 0.894 | 0.850 |
| Testing Phase (N_ = 54, N_+ = 42) | | | |
| Sensitivity (FN) | 90.5% (4) | 95.2% (2) | 73.8% (11) |
| Specificity (FP) | 87.0% (7) | 42.6% (31) | 98.1% (1) |
| AUC | 0.950 | 0.908 | 0.887 |

Interestingly, using the single antigen with the highest t-score (the Mod-C6 like in the IgG membrane) alone as an input to the network, results in an AUC of 0.850 and a sensitivity and specificity of 77.1% and 98.1%, respectively. Such performance for early-stage LD samples is characteristic of EIAs that detect only a single antibody, as the antigen-targets employed, such as the Mod-C6, can be synthesized to limit the presence of cross-reactive epitopes while failing to detect less prevalent antibodies, such as OspC or BmpA that may be produced at the beginning of the infection, albeit at lower concentrations. A significant benefit of the computationally-determined multi-antigen panel is also clearly reflected in the blind testing set, showing the highest AUC when compared to networks trained with the full antigen panel and the Mod-C6 alone (see Table 2).

It is also important to note that the SFFS method implemented in this work, which is referred to as a wrapper feature selection technique, does not simply select the top individual discriminators (i.e., the sensing channels with the highest t-score). Instead, it iteratively adds input features and assesses their performance as an ensemble of inputs to a neural network. It should be emphasized that filtering the input features based on the top nine (9) individual t-scores results in poorer cross-validation performance (AUC=0.900, Sensitivity=79.2%, Specificity=92.3%) when compared to a network with nine (9) features selected by the SFFS method. This can be partly attributed to the relative unimportance of redundant information. In other words, antigen-targets associated with the same patient population or stage of infection as an already implemented antigen-target are of less value to the diagnostic performance, despite having good performance as a single discriminator; in fact, this is a very important conclusion for the design of multiplexed sensors in general, which certainly applies to the early-stage LD xVFA system 4.

Additionally, the positive and negative control spots 72, while not intended for unilaterally discriminating seropositive and negative samples can contain pertinent relative information for a computational POC sensor. For example, the relative concentration of AuNPs 66 in the conjugation pad 58 as well as instances of strong non-specific binding from matrix effects inherent in human sera can be represented by the positive and negative control immunoreactions and thus factored into the logistical classifier.

Alternative to the wrapper SFFS technique used here, a global search could be implemented in which the network is trained by every combination of possible sensing channels. However, this requires training a network for every possible subset of M sensing channels, multiplied by the number of folds in the k-fold cross validation, i.k.

$$k * \sum_{r=1}^{M} \frac{M!}{r!(M-r)!}.$$

With the multiplexed xVFA system 4 (M=20) and 5-fold validation, this results in over 5.2 million training instances, which was prohibitive due to the computation time required (>10,000 hours at 7.2 seconds per training instance on an NVIDIA GeForce FTX1080 Ti GPU).

In addition to the performance advantages discussed above, the feature selection process can also be used to reduce the cost per-test. For example, the reagent cost for the full antigen panel (M=20) would be reduced by 44% by implementing the subset of nine (9) immunoreaction spots selected during the training phase (FIG. 18D). Although not considered here, other methodologies could even incorporate reagent cost into the feature selection cost function, J(y,y') to better illustrate cost-performance trade-offs. Additionally, immunoreaction spots with antigen-targets that were not computationally selected could be replaced in future sensing membrane 70 designs by redundancies of positive and negative control spots as well as already selected capture antigens, or even alternative antigen-targets not yet tested. This type of data-driven iterative assay development is universally applicable, and could be a powerful framework for improving multiplexed sensors, especially for complex diagnoses like LD as well as for POC tests that must balance cost and performance. In addition, this data driven approach can be used to select an optimal panel of antigens that are region and/or population specific based on unique differences in Bb variants in local regions and patient-dependent adaptive immunity. Training on region-specific patient samples can be used to develop multiple region-specific algorithms all used with the same hardware platform to enhance accuracy based on the local patient population.

Optimization of the False-Positive and False-Negative Rate

Another important aspect of the training and feature selection phase is the degree of trade-off between sensitivity and specificity. The diagnostic algorithm can be influenced during the training phase by penalizing instances of false negatives more heavily than instances of false positives, e.g., through tunable weights on the two terms in the binary cross-entropy cost function used to train the network (Eq. 6), or by adjusting the threshold which discriminates between positive and negative samples. In practice, it may be more beneficial for a POC assay that is intended to be used at the first line of patient assessment, to have a greater portion of false positives over false negatives, especially in the case of contagious diseases. However, another important consideration is the pre-test likelihood, which can be low for samples submitted for serological LD testing (<20%). Therefore, it may also be important to ensure a lower portion of false positives in order to reduce the overall number of misdiagnoses. Ultimately however, due to the small number of misclassified samples observed during the training phase in this investigation (only 6), none of these possible adjustments were implemented before the initial blind testing. With larger data-sets, where the empirical effect of tuning the bias can be better modeled, these approaches should be considered and jointly investigated with experts in diagnostic testing.

Batch-Specific Standardization

Although the blind testing sensitivity is comparable to the cross-validation sensitivity during the training phase, indicating that the deep learning-based diagnostic algorithm did not over-fit to the training data-set, the network did exhibit a drift in its numerical output from the training phase to the testing set (see FIGS. 24A-24D). The mean output for negative samples shifted from 0.060±0.156 to 0.278±0.246 (mean±SD) between the training and testing samples (also shown in FIGS. 24A-24D). This effect is likely due to the instability of the antigen-targets, which produced underlying statistical differences of the $R_m$ signals between the training and testing phases of the clinical study, which were conducted three (3) months apart due to sample availability from the LDB. Additionally, differences in temperature and humidity at the time of manual fabrication among other variables can impact repeatability across fabrication batches. Such issues are also pervasive in commercial assays, demanding production-grade equipment to establish environmental controls during automated fabrication as well as rigorous quality assurance to verify performance standards.

To mitigate such issues, future batches of multiplexed immunodiagnostic assay devices 2 can be standardized to sample means ($\overline{R_m}$) and standard deviations ($\sigma_m$) as a characteristic signature of their fabrication batch (see Eq. 4). For example, during the initial blind testing phase reported in this work, the mean and standard deviation of the training data were used for the input standardization. This resulted in a drift of the $R_m'$ inputs away from zero, which can in turn manifest as a drift in the network output. Therefore, by standardizing the blind testing inputs to the sample mean and standard deviation of the testing batch, the drift in negative sample outputs is reduced by over 80% (see FIGS. 24A-24D). As a result, three of the false positive samples are subsequently classified as true negatives (with a decision threshold of 0.5), increasing the specificity from 87.0% to 92.6% and the AUC from 0.950 to 0.963 with respect to the two-tier serology, while only incurring one extra false negative sample. Practically, batch-specific sample means and standard deviations could be calculated as a running average of the activated devices 2 in a batch, and could even be exclusively determined using endemic control sera, which is more readily available. An alternative approach is to include fabrication batch information as inputs to the network in the form of external labels. In this case, the network could learn inherent batch-to-batch variations and compensate for these differences through its internal tunable parameters.

The multiplexed immunodiagnostic assay device 2 is capable of diagnosing early-stage LD at the POC. The multiplexed immunodiagnostic assay device 2 has a material cost of ~$0.42 per-test and can be performed in 15 min by an individual with minimal training. A low-cost and hand-held portable reader device 10 enables automated analysis to quantify colorimetric signals generated on a nitrocellulose sensing membrane 70, followed by analysis with a neural network for inferring a diagnosis from the multi-antigen sensing information. By computationally selecting a panel of detection antigens for IgM and IgG antibodies specific to LD and performing a fully-blinded clinical study with early-stage LD samples, the multiplexed immunodiagnostic assay device 2 was shown to have an AUC, sensitivity, and specificity of 0.950, 90.5%, and 87.0%, respectively, with respect to the two-tier serological testing. Using batch-specific standardization and threshold tuning, the specificity of the blind-testing performance was improved to 96.3%, with an AUC and sensitivity of 0.963 and 85.7%, respectively.

The multi-target and POC nature of the computational multiplexed immunodiagnostic assay device 2 make it uniquely suited for LD diagnostics, presenting major advantages in terms of time, cost, and performance when compared to (first-tier) EIAs with single antigen-targets as well as standard two-tier testing methods that are rather costly (e.g., >$400/test) and slow (>24 hours for results). In another embodiment, rather than having first and second cassettes 40a, 40b, a single cassette 40 can be used for measuring IgM and IgG antibodies in a single test. Additionally, the computational framework outlined here can be used for iteratively designing more competitive versions of the multiplexed immunodiagnostic assay device 2 that incorporate statistically more stable, sensitive, and specific capture molecules such as synthetic peptides with epitopes engineered for high capture-affinity and low cross-reactivity.

While embodiments of the present invention have been shown and described, various modifications may be made without departing from the scope of the present invention. For example, while the invention has been described as using color images, the assay device may also function using monochrome images. In addition, while the assay 2 and system 4 was described largely in the context of diagnosing early stage Lyme disease, the assay may be used with other diseases and conditions. Also, the particular composition, order and sequence of the various stack of porous layers 54 may vary. The invention, therefore, should not be limited except to the following claims and their equivalents.

What is claimed is:

1. A multiplexed immunodiagnostic assay device comprising:
   one or more cassettes each cassette having a lower portion, a first upper portion and a second upper portion, wherein the lower portion of the one or more cassettes contains a sensing membrane having a plurality of immunoreaction spots or locations formed therein, and wherein the first upper portion and the second upper portion are each detachably connected to the lower portion of the one or more cassettes and configured to receive a sample or assay solution, wherein the first upper portion comprises a stack of discrete porous layers including one or more vertical flow diffuser layers and wherein the second upper portion comprises a stack of discrete porous layers including at least one conjugation pad layer holding antibody-conjugated nanoparticles therein; and
   a portable reader device having one or more illumination sources and at least one processor or control circuitry, a camera, wherein the one or more illumination sources configured to illuminate the sensing membrane in the lower portion of the one or more cassettes and the camera captures color or monochrome images of the sensing membrane.

2. The multiplexed immunodiagnostic assay device of claim 1, wherein the first upper portion comprises a stack of porous paper, glass fiber, cotton, and/or polymer layers comprising at least one absorption layer, one or more vertical flow diffuser layers, one or more spreading layers, and at least one supporting layer and wherein the second upper portion comprises a stack of porous paper, glass fiber, cotton and/or polymer layers comprising at least one absorption layer, one or more vertical flow diffuser layers, one or more spreading layers, at least one conjugation pad layer holding the antibody-conjugated nanoparticles therein, and at least one supporting layer.

3. The multiplexed immunodiagnostic assay device of claim 1, wherein the portable reader device comprises an opto-mechanical attachment and a mobile phone or other portable electronic device and wherein the camera comprises the camera of the mobile phone or other portable electronic device.

4. The multiplexed immunodiagnostic assay device of claim 1, wherein the portable reader device comprises an opto-mechanical attachment configured to attach to a mobile camera or other portable electronic device and the opto-mechanical attachment contains at least one processor contained therein configured to execute one or more of image processing software or analysis software.

5. The multiplexed immunodiagnostic assay device of claim 1, further comprising a computing device or at least one processor configured to process the color or monochrome images to calculate a k/s statistic per sensing spot or location.

6. The multiplexed immunodiagnostic assay device of claim 5, the computing device or at least one processor configured to output a k/s image of the sensing membrane.

7. The multiplexed immunodiagnostic assay device of claim 1, further comprising a local or remote computing device configured to execute a trained neural network configured to receive one or more of (i) monochrome or color images obtained by the camera of the portable reader device or (ii) normalized pixel intensity values for one or more of the immunoreaction spots or locations and generate a diagnostic decision comprising at least a positive (+) or negative (−) indication for the sample.

8. The multiplexed immunodiagnostic assay device of claim 7, wherein the trained neural network is trained to further infer or output a concentration of at least one disease marker of interest in the sample.

9. The multiplexed immunodiagnostic assay device of claim 8, wherein the trained neural network is trained with a plurality of different biomarkers including disease-specific antigens, antibodies, and positive/negative controls.

10. The multiplexed immunodiagnostic assay device of claim 9, wherein the plurality of different biomarkers comprises Lyme disease-specific antigens and/or antibodies.

11. The multiplexed immunodiagnostic assay device of claim 10, wherein the plurality of different biomarkers comprise one or more of OspC, BmpA, P35, P41, DbpB, Crsasp1, ErpD, Mod-C6, and anti-Human IgG/IgM.

12. The multiplexed immunodiagnostic assay device of claim 1, wherein the conjugation pad further comprises one or more of fluorescent molecules or dyes, enzymes, proteins or protein fragments, nucleic acids, nanometer or micrometer-sized particles, or other labeled biomolecules.

13. The multiplexed immunodiagnostic assay device of claim 1, wherein the plurality of immunoreaction spots or locations are separated from one another by one or more physical barriers or hydrophobic barrier material located in the sensing membrane.

14. The multiplexed immunodiagnostic assay device of claim 5, wherein the computing device comprises a remote or local computing device operatively connected to or interfacing with the portable reader device.

15. The multiplexed immunodiagnostic assay device of claim 5, wherein the computing device comprises the mobile phone or other portable electronic device.

16. The multiplexed immunodiagnostic assay device of claim 1, wherein the one or more vertical flow diffuser layers comprises one or more porous membrane(s) having a plurality of concentric wax or hydrophobic barriers formed therein.

17. The multiplexed immunodiagnostic assay device of claim 1, wherein the first upper portion and the second upper portion of the one or more cassettes are each detachably connected to the lower portion by twisting the respective upper portions onto the lower portion.

18. The multiplexed immunodiagnostic assay device of claim 17, wherein the lower portion of the one or more cassettes is detachably connected to the portable reader device by twisting the lower porting onto the portable reader device.

19. A method of using the multiplexed immunodiagnostic assay device of claim 1 comprising:
  securing the first upper portion to the lower portion of one of the one or more cassettes;
  flowing one or more buffer solutions into an inlet of the first upper portion along with a solution containing the sample;
  removing the first upper portion from the lower portion;
  securing the second upper portion to the lower portion;
  flowing a buffer or wash solution into an inlet of the second upper portion;
  removing the second upper portion from the lower portion;
  inserting the lower portion with the sensing membrane into or onto the portable reader device;
  illuminating the sensing membrane and capturing one or more color or monochrome images of the sensing membrane;
  subjecting the captured one or more color or monochrome images to image processing with a computing device or at least one processor to generate a normalized pixel intensity value or k/s statistic for the immunoreaction spots or locations on the sensing membrane; and
  outputting a result indicating a positive (+) or negative (−) classification for the sample based on the k/s statistic for the immunoreaction spots or locations on the sensing membrane.

20. The method of claim 19, further comprising outputting a concentration or concentration range of one or more biomarkers based on the normalized pixel intensity value or k/s statistic for the immunoreaction spots or locations on the sensing membrane.

21. A method of using the multiplexed immunodiagnostic assay device of claim 1 comprising:
  securing the first upper portion to the lower portion of one of the one or more cassettes;
  flowing one or more buffer solutions into an inlet of the first upper portion along with a solution containing the sample;
  removing the first upper portion from the lower portion;
  securing the second upper portion to the lower portion;
  flowing a buffer or wash solution into an inlet of the second upper portion;
  removing the second upper portion from the lower portion;
  inserting the lower portion with the sensing membrane into or onto the portable reader device;
  illuminating the sensing membrane and capturing one or more color or monochrome images of the sensing membrane;
  subjecting the captured one or more color or monochrome images to image processing with a computing device to generate normalized pixel intensity values for one or more of the immunoreaction spots or locations; and inputting the normalized pixel intensity values for the one or more of the immunoreaction spots or locations to a trained neural network configured to receive the same and generate a confidence score reflective of at least a positive (+) or negative (−) indication for the sample based on a thresholding of the confidence score.

22. The method of claim 21, wherein the computing device performing image processing comprises a remote or local computing device operatively connected to the portable reader device, mobile phone, or other portable electronic device.

23. The method of claim 21, further comprising transferring the normalized pixel intensity values to a remote or local computing device that executes the trained neural network.

24. A method of using the multiplexed immunodiagnostic assay device of claim 1 comprising:
 securing the first upper portion to the lower portion of one of the one or more cassettes;
 flowing one or more buffer solutions into an inlet of the first upper portion along with a solution containing the sample;
 removing the first upper portion from the lower portion;
 securing the second upper portion to the lower portion;
 flowing a buffer or wash solution into an inlet of the second upper portion;
 removing the second upper portion from the lower portion;
 inserting the lower portion with the sensing membrane into or onto the portable reader device;
 illuminating the sensing membrane and capturing one or more color or monochrome images of the sensing membrane;
 subjecting the captured one or more color or monochrome images to image processing with a computing device to generate normalized pixel intensity values for one or more of the immunoreaction spots or locations; and
 inputting the normalized pixel intensity values for the one or more of the immunoreaction spots or locations to a trained neural network configured to receive the same to a trained neural network configured to output a concentration of at least one disease marker of interest.

* * * * *